US012661265B2

(12) United States Patent
Vogelsang et al.

(10) Patent No.: US 12,661,265 B2
(45) **Date of Patent: \*Jun. 23, 2026**

(54) UV-LASER-BASED SYSTEM FOR CORRECTING IMPAIRED VISION, AND METHOD FOR CENTERING SAME

(71) Applicant: Carl Zeiss Meditec AG, Jena (DE)

(72) Inventors: Hartmut Vogelsang, Oberweser (DE); Christian Deutsch, Weimar (DE); Ingo Wundrich, Weimar (DE); Dan Zoltan Reinstein, London (GB)

(73) Assignee: Carl Zeiss Meditec AG, Jena (DE)

( \* ) Notice: Subject to any disclaimer, the term of this patent is extended or adjusted under 35 U.S.C. 154(b) by 791 days.

This patent is subject to a terminal disclaimer.

(21) Appl. No.: 17/996,808

(22) PCT Filed: May 21, 2021

(86) PCT No.: PCT/EP2021/063615
§ 371 (c)(1),
(2) Date: Oct. 21, 2022

(87) PCT Pub. No.: WO2021/239605
PCT Pub. Date: Dec. 2, 2021

(65) Prior Publication Data
US 2023/0181365 A1 Jun. 15, 2023

(30) Foreign Application Priority Data

May 24, 2020 (DE) .................... 10 2020 206 423.7
May 24, 2020 (DE) .................... 10 2020 206 424.5
(Continued)

(51) Int. Cl.
*A61F 9/00* (2006.01)
*A61F 9/008* (2006.01)

(52) U.S. Cl.
CPC .............................. *A61F 9/00804* (2013.01); *A61F 2009/00846* (2013.01); *A61F 2009/00872* (2013.01)

(58) Field of Classification Search
CPC ........ A61F 9/00804; A61F 2009/00846; A61F 2009/00872
See application file for complete search history.

(56) References Cited

U.S. PATENT DOCUMENTS 7,480,396 B2 \* 1/2009 Teiwes .................... A61F 9/008
351/240
8,852,176 B2 \* 10/2014 Riedel ................. A61F 9/00825
606/4
(Continued)

FOREIGN PATENT DOCUMENTS

CN 102811684 A 12/2012
CN 103501686 A 1/2014
(Continued)

OTHER PUBLICATIONS

Krueger et al.: "Corneal Surface Morphology Following Excimer Laser Ablation With Humidified Gases," Archives of Ophthalmology, vol. 111, No. 8, pp. 1011-1152, Aug. 1993.
(Continued)

*Primary Examiner* — Shirley X Jian
(74) *Attorney, Agent, or Firm* — Pearl Cohen Patentanwälte PartGmbB; Michael McCandlish

(57) ABSTRACT

A UV-laser-based system (UVL-LVC system) for correcting the impaired vision of a patient's eye has a UV-laser source, which emits laser radiation to treat the patient's eye, and imaging optics for focusing the laser radiation onto the cornea of the patient's eye. The imaging optics allow a detection of a reflection of radiation, which is emitted onto the cornea of the patient's eye with the imaging optics and is at least partly reflected by the cornea of the patient's eye (Continued)

back into the imaging optics at an acceptance angle $\chi_{Max}$ of at least 2.5°. Additionally a method for centering a UVL-LVC system is disclosed.

48 Claims, 13 Drawing Sheets

(30) Foreign Application Priority Data

| May 24, 2020 | (DE) | .................... | 10 2020 206 425.3 |
| Jul. 10, 2020 | (DE) | .................... | 10 2020 208 676.1 |

(56) References Cited

U.S. PATENT DOCUMENTS

| 9,592,156 | B2 | | 3/2017 | Huang | |
| 9,918,873 | B2 | * | 3/2018 | Woodley | ............ G01B 9/02091 |
| 10,849,789 | B2 | * | 12/2020 | Dewey | ................... A61B 3/103 |
| 11,672,419 | B2 | * | 6/2023 | Dewey | ................. A61B 3/0025 |
| | | | | | 606/4 |
| 11,911,104 | B2 | * | 2/2024 | Gonzalez | ............... A61B 3/107 |
| 2002/0026180 | A1 | * | 2/2002 | Nakamura | .......... A61F 9/00804 |
| | | | | | 606/5 |
| 2002/0128634 | A1 | | 9/2002 | Donitzky et al. | |
| 2005/0024586 | A1 | * | 2/2005 | Teiwes | ................... A61B 3/113 |
| | | | | | 351/209 |
| 2008/0242965 | A1 | | 10/2008 | Norris et al. | |
| 2009/0242021 | A1 | * | 10/2009 | Petkie | .................. H10F 77/315 |
| | | | | | 136/256 |
| 2011/0040292 | A1 | * | 2/2011 | Riedel | ................. A61F 9/00802 |
| | | | | | 606/5 |
| 2011/0149241 | A1 | * | 6/2011 | Dai | ..................... A61F 9/00819 |
| | | | | | 351/205 |
| 2011/0202046 | A1 | | 8/2011 | Angeley et al. | |
| 2012/0265181 | A1 | | 10/2012 | Frey | |
| 2013/0226157 | A1 | | 8/2013 | Huang | |
| 2015/0116725 | A1 | * | 4/2015 | Lemonis | ............ G01B 9/02049 |
| | | | | | 356/479 |
| 2015/0141972 | A1 | * | 5/2015 | Woodley | ............. A61F 9/00804 |
| | | | | | 606/5 |
| 2016/0095752 | A1 | * | 4/2016 | Srinivasan | .......... A61F 9/00834 |
| | | | | | 606/6 |
| 2017/0189233 | A1 | * | 7/2017 | Dewey | ................ A61F 9/00825 |
| 2019/0314202 | A1 | * | 10/2019 | Mordaunt | ........... A61F 9/00812 |
| 2023/0181365 | A1 | * | 6/2023 | Vogelsang | .......... A61F 9/00804 |
| | | | | | 606/3 |
| 2023/0201035 | A1 | * | 6/2023 | Vogelsang | .............. A61F 9/009 |
| | | | | | 606/5 |

FOREIGN PATENT DOCUMENTS

| DE | 102009030464 | A1 | 12/2010 |
| WO | 2010028663 | A1 | 3/2010 |
| WO | 2010/149300 | A1 | 12/2010 |

OTHER PUBLICATIONS

Atchison, "Handbook of Visual Optics vol. 1," Chapter 17, Ed. Pablo Artal, CRC Press Tayler & Francis Group, 2017.

International Preliminary Report on Patentability issued in PCT/EP2021/063615, to which this application claims priority, mailed Nov. 17, 2022, and English-language translation thereof.

Office Action by the Chinese Patent Office (CIPO) issued in CN 202180037534.X, which is a counterpart hereof, mailed on Jun. 27, 2025, and English-language machine translation thereof.

Nowakowski et al.: "Investigation of the isoplanatic patch and wavefront aberration along the pupillary axis compared to the line of sight in the eye," Biomedical Optics Express 240, vol. 3, No. 2, Feb. 1, 2012.

International Search Report by the International Searching Authority in PCT/EP2021/063615, to which this application claims priority, mailed Sep. 6, 2021, and English-language translation thereof.

Written Opinion by the International Searching Authority in PCT/EP2021/063615, to which this application claims priority, mailed Sep. 6, 2021.

Office Action by the European Patent Office (EPO) issued in EP 21 728 513.9, which is a counterpart hereof, mailed on Jun. 18, 2025, and English-language machine translation thereof.

U.S. Appl. No. 17/996,814, filed Oct. 21, 2022, Hartmut Vogelsang, Dan Z. Reinstein Christian Deutsch, and Ingo Wundrich.

Notice of Issuance issued in CN 202180037534.X, which is a counterpart hereof, mailed on Jan. 26, 2026, and English-language machine translation thereof.

* cited by examiner

UV-LASER-BASED SYSTEM FOR CORRECTING IMPAIRED VISION, AND METHOD FOR CENTERING SAME

CROSS REFERENCE TO RELATED APPLICATIONS

This application is a national stage application of international patent application PCT/EP2021/063615, filed May 21, 2021, designating the United States and claiming priority from German patent applications DE 10 2020 206 423.7, filed May 24, 2020, DE 10 2020 206 424.5, filed May 24, 2020, DE 10 2020 206 425.3, filed May 24, 2020, and DE 10 2020 208 676.1, filed Jul. 10, 2020, and the entire content of all applications is incorporated herein by reference.

TECHNICAL FIELD

The present disclosure relates to ultraviolet laser-based (UVL) laser vision correction (LVC) systems, that is to say systems for vision correction by means of laser radiation, with the correspondingly included treatment laser emitting in the ultraviolet range, such as for example an excimer laser or solid-state laser with wavelengths between approximately 193 nm and 213 nm. These systems are typically pulsed systems, that is to say not systems that emit continuous waves (cw). Such UVL-LVC systems are used to process the cornea of a patient's eye starting from its surface (e.g., PRK, LASEK) or to process a volume under a folded-away surface of the cornea of the patient's eye starting from the exposed surface (LASIK), in each case by means of photoablation. The disclosure furthermore relates to corresponding methods for UVL-LVC systems.

BACKGROUND

Conventional UVL-LVC systems, for example the MEL systems by Carl Zeiss Meditec AG, the systems Amaris by Schwind eye-tech solutions GmbH or the Micron systems by Excelsius Medical GmbH, are systems for vision correction that have been successfully employed for a long time. The present disclosure proposes and explains further improvements for such systems.

Conventional UVL-LVC systems typically provide for a rigid laser beam guiding system. Although this facilitates safe laser beam guidance, it requires that the patient on a patient couch is moved under a fixed system aperture in x, y, z coordinates by means of said patient couch until the patient's eye intended to be treated is correctly positioned in relation to the optical axis of the system. An exception is formed by the system described in US 2013/0226157 A1, in which the laser arm, rigid per se, is positioned as a whole over the patient, albeit in a manner which still requires the positioning of the patient by way of the patient couch. For safety reasons, the latter frequently requires the patient couches to be electrically and/or mechanically connected to the laser base unit, which in turn requires a system certification and large amounts of space.

Additionally, there usually is a manual, static alignment of the eye in relation to cyclorotation in conventional UVL-LVC systems, i.e., without an automatic correction with the aid of registration data, by rotating the patient's head on the couch under visual monitoring. This limits the obtainable accuracy and may then lead to unwanted deviations if there is a rotation of the head of the patient during the treatment without a correction of the cyclorotation caused thereby.

Moreover, contact interfaces for affixing the eye are known in some conventional UVL-LVC systems. In such UVL-LVC systems, for example as described in US 2013/0226157 A1 and U.S. Pat. No. 9,592,156 B2, these are only implemented for eye stabilization purposes and do not adopt an active role. By contrast, work is carried out entirely without contact interfaces in many systems.

Large working distances between laser exit aperture and eye were realized with the introduction of spot-scanning UVL-LVC systems. This was also implemented against the background of using microkeratomes, which were used with the patient on the patient bed of the system, in order to cut the LASIK flap, that is to say an opening in the cornea that can be folded to one side. Among other things, this also required great working distances. Eye trackers for registering and compensating the eye movements were introduced at a later stage, and hence the eye movements during the ablation were compensated since the eye is not affixed. The overall optical system concept accompanying this—which in principle is very similar in the various systems—may also be considered to be disadvantageous.

Various technical challenges arise in relation to eye tracking during the application. Overall, the registration speed for the eye movement is limited and the adjustment of the scanner mirrors for correcting the pulse coordinate requires a finite amount of time. In the context of the system performance, the response to the eye movement ("response time") is generally delayed and hence limited in terms of accuracy. In the case of conventional, fast eye tracker systems (with the repetition rate of approximately 1000 Hz), this is sufficient for the lateral correction (x, y displacement; "1st and 2nd eye tracking dimension"). However, even the fastest conventional systems may lead to limitations, especially if the eye tracker speed is below the limit for the scanning frequency. In some systems, a prediction about the future movement of the eye is made on the basis of the preceding movement trajectories of the eye ("7th eye tracking dimension"). However, this is only possible within the scope of an approximation since eye saccades/nystagmus correspond to statistical movements of the eye in the broadest sense. This also highlights the fact that an increase in the repetition rate is connected with technical challenges with conventional technologies, even though this would be of interest for certain applications and in certain ablation timeframes (thermal controlled/mild ablation).

Moreover, purely lateral tracking can be a limitation since the rotation of the eye about the z-axis ("dynamic cyclorotation;" "6th eye tracking dimension") and the roll movements about the horizontal and vertical eye axes ("3rd and 4th eye tracking dimension") have to be taken into account to achieve a best-possible accuracy. Moreover, the distance (z-distance) to the laser exit aperture may also vary, which can likewise be compensated for by appropriate tracking (5th eye tracker dimension).

Despite all technical intricacies and correction options, the conventional systems are limited in reacting exactly to a change in the eye position in some cases: The limited quality of the registration and the speed of the registration and correction may have a decisive influence in this case. However, the influence on the refractive results is normally very small and hardly detectable.

However, further challenges may arise with the eye tracking in the case of uncooperative patients, in the case of whom there are fixation instability, nervousness, cognitive deficits or problems with perceiving the fixation target. In some cases, it may appear necessary to the eye surgeons to manually affix the eyes of the patient during the ablation by means of a clamp and/or a foam spatula in order to enable a precise ablation. This may serve to prevent an eye movement outside of what is known as the (limited) "eye tracker hot zone" because the system may otherwise have to be stopped.

In the case of UVL-LVC systems, too, it is necessary to always ensure that the production of prismatic errors by way of the eye tracker is avoided. If this is not ensured, this may lead to the unwanted case of the ablation profiles not being applied in the correct plane, that is to say not on the surface normal, i.e., perpendicular to the visual axis. This may be promoted by virtue of the patient preferably fixating in a largely fixed but "incorrect" direction, that is to say, e.g., permanently looking in a fixed direction that does not correspond to the center of the "fixation cloud" (depending on refractive deficit and treatment duration, the patient can no longer see the fixation target in focus during the operation).

FIG. 1 shows a schematic representation of the principle of how prismatic correction errors (tip/tilt) arise as a result of the insufficiently accurate use of an eye tracker when the patient does not fixate on the center of the "fixation cloud." In this case, FIG. 1 depicts a patient's eye 10 with cornea 12 and fovea 14, and the optical axis 16 of the patient's eye or the visual axis 16, an ablation profile 18, a scanning system 20, and a fixation element 22, on which the patient should fixate with their gaze.

If the patient does not fixate their eye 10 on the center but, for example, on an edge region of the fixation element 22, this may have as a consequence that the ablation profile 18 is not correctly applied along the necessary treatment axis (e.g., visual axis 16; defined by the ophthalmic pole (OP) and fixation of the patient) and hence not applied normally with respect to the visual axis. The relationships are depicted with much exaggeration in FIG. 1.

Eye trackers do not equally reliably function for all eyes either since some eye colors may have an insufficient contrast. Should the use of the eye tracker not be possible, eye surgeons may be compelled to terminate the operation or continue without eye-tracker assistance, but this places greater demands on the capabilities of the surgeon and/or may impair the quality of the treatment results under certain circumstances.

Constant ambient conditions above the operation site often cannot be set, or can only be set to a very qualified extent, in conventional systems. However, it is known that the influence of varying ambient conditions, for instance air humidity and changes in the hydration state of the cornea accompanying this, the composition of the air (in the case of evaporation of solvents for example) or the temperature, on the refractive results may be significant. It is also known that it is advantageous to ensure that the hydration state of the cornea is maintained during the ablation, or to avoid drying out of said cornea (see, e.g., R. R. Krueger, M. Campos, X. W. Wang, M. Lee, P. J. McDonnell, "Corneal Surface Morphology Following Excimer Laser Ablation With Humidified Gases," Arch Ophthalmol. 111, 1993). Typically, a distinction should be made between two effects for the hydration: a) the physiological differences in the hydration of the cornea as a distribution over various patients, and b) the maintenance of the hydration during the ablation itself. Both influences lead to an increased variation in the refractive result (for example via an increased variation in the "attempted vs. achieved" prediction). The literature contains many investigations in this respect. Accordingly, the influence of the hydration of the cornea is significant in particular.

A further factor that influences the refractive results is related to the amount and accumulation of ablation products ("debris") over the ablated cornea, that is to say the operation site. It is sufficiently well known that the radiated-in UV ablation pulses may be absorbed and scattered in the debris. This may uncontrollably modify the effective pulse fluence, which decisively controls the ablation process. This may lead to significant fluence deviations in the sequence of the ablation pulses. In the case of myopia treatments, this may lead to the unwanted creation of central steepening of the cornea post surgery (what are known as central islands). Therefore, conventional systems usually have an aspiration means or a combined air supply and aspiration means for the debris. However, a large distance from the supply or discharge lines may be an obstacle to an effective removal of the debris. In principle, a replacement of the entire air volume above the treated cornea between successive pulses in the case of pulse repetition rates between 500 Hz and 1000 Hz would be advantageous to this end. Otherwise, this may lead to "skew" ablations and hence, for example, to induced coma or SIA (surgically induced astigmatism)—in the case of non-optimal or directed aspiration of the ablation products—which should be avoided.

The sterile and secure placement of the flap is of extraordinary importance for a LASIK procedure. Typically, a flap is only 100 μm thick and, following the LASIK incision, only fastened to the cornea by way of a very narrow "hinge." Maintaining the hydration of the flap is very important for pathological reasons but also for maintaining the shape of the flap since dehydrated flaps may shrink within seconds. Under certain circumstances, a shrunken flap may suffer from accuracy of fit in relation to the stromal bed post treatment (which may also be due to the change in shape of the stroma surface by the ablation), which may lead to postsurgical complications (e.g., "epithelial ingrowth") if not given due consideration. Where possible, flaps should not be bent, pulled or otherwise stressed either. Hence, experts these days hardly still use the "calzone technique" that was employed in the past. Moreover, the flap should also be prevented from coming to rest in possibly non-sterile regions of the eye. Despite the sterile preparation of the eye, this may occur, for example as a result of the tear film or contact with non-sterile parts of the lids.

In want of a solution that is integrated in the conventional systems, some users cut their own flap repositories from sterile foam spatulas (or similar material), which are then moistened and serve as safe and sterile rest for the sensitive flap. Thus, a solution is sought after in order to improve this.

On account of the relatively large working distances A of conventional UVL-LVC systems, there is hardly a difference there in the focusing plane. Therefore, these UVL-LVC systems can be considered to be virtually telecentric on the image side. In the case of conventional UVL-LVC systems, which typically have a working distance (distance between equipment exit aperture contour and eye) of approximately 250 mm, the rays are incident on the cornea at a significant angle since the typical radius of curvature RC of the human eye is approximately 7.86 mm. This has the further disadvantage that the optical acceptance angle for the return of reflections at the cornea to the optical system is also very small, leading to significant limitations of current systems and, as a rule, precluding, or reducing to a minimum, a use of the reflections at the cornea.

Now, further disadvantages of conventional UVL-LVC systems are described, which result largely directly from the optical concepts and the geometry of the ablation resulting therefrom.

As a result of an oblique incidence of the laser radiation on the cornea, there are losses in the fluence, that is to say the energy density of the laser pulse, which is decisive for the ablation, in conventional systems. Two effects should be considered here: The losses from deviations of the pulse ablation footprint as a result of the local geometry of the cornea at the location of the ablation pulses ("geometry factor") and the Fresnel losses when radiating light at interfaces with different refractive index (air, cornea), which can be calculated using the Fresnel equations. These effects are sufficiently well known in the related art.

The pulse ablation shape (corresponds to the ablation-effective fluence distribution of the radiated-in ablation laser pulse in a plane perpendicular to the direction of incidence) is deformed by the geometry of the irradiation on the cornea to form the "pulse ablation footprint on cornea," and hence the fluence distribution changes vis-à-vis the radiated-in "pulse ablation shape."

The Fresnel losses can be calculated with the aid of the Fresnel equations with knowledge of the refractive indices of the air and cornea (or stroma) and the angles of incidence, with the polarization of the laser radiation having to be taken into account.

The use of back reflections from the cornea of the patient's eye for analysis purposes and, in particular, for centration purposes is only possible to a very restricted extent, or even entirely impossible, on account of the large working distance of conventional UVL-LVC systems from the patient's eye and the small acceptance angle of the focusing optical unit accompanying this. The influence of inaccurate centration is known and has already been discussed multiple times in the literature. The view often taken that centration errors, that is to say deviations of the ablation center from the target positions on the cornea, like typically by the "ophthalmic pole" for centration on the visual axis, which are referred to as decentrations below, would have no influence on spherical corrections is physically applicable only in certain cases, for example spherical corrections on spherical corneas. However, the visual physiology, inter alia, is not considered in this case. As a rule, decentrations may lead to a displacement in the physiological visual axis. When processing the visual impression in the brain, the eye is "rotated" by the eye muscles such that the light continues to fall on the point of sharpest vision, which in principle compensates the prismatic offset ("tip/tilt"). This may lead to problems in the case of binocular vision (stereopsis), for example, which problems are known from investigations in relation to insufficiently centrated spectacle lenses, for example. Particularly in the case of aspherical corrections on ellipsotoric corneas, which corresponds to the real, actual scenario, a decentration may also lead purely physically to a non-attainment of the sought-after correction. Accordingly, decentrations may have a significant influence on the results of "customized ablation," as this thus leads to the induction of higher aberrations ("night vision complaints," etc.) and hence also to the influence on the refractive result. Hence, a centration that is as exact as possible is therefore paramount for a good result in the case of both topography and wavefront corrections.

Aberrations (or optical modes) couple under decentration. As a result of sphere and cylinder coupling to higher-order aberrations (coma, spherical aberration, higher-order astigmatisms), including those occurring in natural (aspherical) eyes, decentrations in real eyes are often critical, even in the case of purely spherocylindrical corrections. By way of example, in the case of a decentration, coma couples to astigmatism and defocus or spherical aberration couples to coma, astigmatism and defocus. A few examples should be provided here, which initially only reveal the effects for the primary aberrations (up to 4th order). The calculations follow from the coordinate transformation of optical modes:

A displacement of 0.25 μm with coma $Z(3,1)$ by 0.3 mm leads to a defocus of approximately $-\frac{1}{8}$ dpt.

A displacement of 0.25 μm with coma $Z(3,1)$ by 0.3 mm (horizontal/vertical) leads to a cardinal astigmatism $(Z(2,2)/(Z(2,-2))$ of $\frac{1}{8}$ dpt.

A displacement of 0.5 μm with coma $Z(3,1)$ by 0.5 mm leads to a defocus of approximately −0.3 dpt.

A displacement of 0.4 μm with coma $Z(3,1)$ by 0.5 mm (horizontal/vertical) leads to a cardinal astigmatism $(Z(2,2)/(Z(2,-2))$ of 0.3 dpt.

A displacement of 0.6 μm with spherical aberration $Z(4,0)$ by 0.4 mm leads to a defocus of approximately $-\frac{1}{8}$ dpt.

A displacement of 0.6 μm with spherical aberration $Z(4,0)$ by 0.4 mm (horizontal/vertical) leads to a cardinal astigmatism $(Z(2,2)/(Z(2,-2))$ of approximately $\frac{1}{8}$ dpt.

Until now, only optical modes manifesting themselves in ablation profiles in the optical zone were considered. The transition zones have not yet been mentioned. However, in this context decentrations also mean that transition zones may reach into the optically active zone, especially in the case of hyperopia corrections. This may then lead to impairments (known as "night vision complaints post surgery;" this does not refer to night myopia), especially in the case of mesopic to scotopic light conditions, and may accordingly be accompanied by patient dissatisfaction.

Pupil centrations (centration in relation to the CSC, "corneal sighting center") can be brought about well and reliably in refractive surgery by means of eye tracking systems ("eye tracker") as integrated pupil recognition. However, this type of centration is not the preferred choice since it has in the meantime been settled in the art that a centration in relation to the ophthalmic pole (visual axis, coaxially sighted corneal light reflex, "CSCLR" condition, see below) or in relation to the vertex would be correct and preferable to a pupil centration. Experience has shown that small and medium myopia corrections are very uncritical in this case. Relatively large astigmatisms and myopia corrections and, in particular, hyperopia corrections are more difficult. This is because hyperopic eyes are typically characterized by a non-negligible angle between the pupillary axis and the visual axis ("angle kappa"). In this case, corneal sighting center and ophthalmic pole are no longer sufficiently close together, leading to a difference between an "angle lambda" and an "angle kappa." As a rule, the angle lambda denotes the angle between the pupil axis or pupillary axis and the "line of sight" and the angle kappa denotes the angle between the pupillary axis and the "visual axis." In this respect, see "Handbook of Visual Optics Vol. 1," CRC Press Taylor & Francis Group, Ed. Pablo Artal, Vol 1, Chapter 17 (by D. A. Atchison), or "Investigation of the isoplanatic patch and wavefront aberration along the pupillary axis compared to the line of sight in the eye," M. Nowakowski, M. Sheehan, D. Neal, A. V. Goncharov, Biomedical Optics Express, Vol. 3, 2. Moreover, the pupil and the pupil center are not fixed points which could unequivocally be provided with a marking. Both the pupil and the pupil center may vary with the lighting conditions.

SUMMARY

It is therefore an object of the present disclosure to describe apparatuses and a method which address the aforementioned problems of currently used UVL-LVC systems.

In particular, it is an object of the disclosure to describe apparatuses and methods for easy and reliable centration of the patient's eye in relation to the UVL-LVS system.

This object is achieved by the apparatuses and methods utilizing an imaging optical unit configured to allow a detection of a back reflection. Exemplary embodiments are specified in the description below.

A first exemplary embodiment of the disclosure relates to a UV laser-based system for vision correction, UVL-LVC system, for a patient's eye. The UVL-LVC system comprises a UV laser source which is designed to emit laser radiation for treating the patient's eye and an imaging optical unit for focusing the laser radiation on the cornea of the patient's eye. In this case, the imaging optical unit is designed such that the imaging optical unit allows a detection of a back reflection of radiation radiated on the cornea of the patient's eye by the imaging optical unit and at least partially reflected by the cornea of the patient's eye, within an acceptance angle $\chi_{Max}$ of at least 2.5°.

A further exemplary embodiment of the disclosure relates to a method for centering a UVL-LVC system for vision correction for a patient's eye. In this case, the method comprises radiating a centration beam on the cornea of the patient's eye by an imaging optical unit, and detecting a back reflection of a part of the radiated-in centration beam reflected by the cornea by means of the imaging optical unit, the back reflection being detected in an angular range of at least 2.5°. Moreover, the method comprises determining a positioning and/or orientation of the UVL-LVC system relative to the patient's eye on the basis of the detected back reflection. Optionally, the centration can be carried out in manual, partly automated or fully automated fashion.

In this case, the imaging optical unit for focusing the laser radiation on the cornea of the patient's eye firstly fulfills the functionality of a focusing optical unit, by means of which a laser beam to be radiated on the patient's eye can be focused on the patient's eye, and secondly fulfills the functionality of at least partly collecting the back reflection reflected by the cornea and of making said back reflection available to the UVL-LVC system. The focusing by the imaging optical unit need not necessarily result in a punctiform or Gaussian focus, but may also produce a focal field with any other shape. The imaging optical unit can optionally be designed to generate a curved focal field.

In this case, the back reflection of the radiation from the cornea optionally is the radiation which is reflected by the surface of the cornea facing the UVL-LVC system and which is at least partially cast back in the direction of the UVL-LVC system. Optionally, the back reflection of the radiation can be the first Purkinje image and/or any further Purkinje image.

The radiation radiated on the cornea of the patient's eye by the imaging optical unit, which is reflected as back reflection, may, but need not necessarily, correspond here to the laser radiation provided by the UV laser source. Alternatively or in addition, the radiated-in radiation may also be provided in the form of a centration beam and/or a scanning beam, with these being provided by a separate laser source, optionally in a different spectral range to the ultraviolet spectral range, for instance in the visible or infrared spectral range. Alternatively or in addition, the radiated-in radiation may also be provided by the UV laser source and for instance correspond to the treatment laser beam with attenuated power.

The imaging optical unit allowing a detection of the back reflection in an acceptance angle $\chi_{Max}$ of at least 2.5° means that the acceptance range detects rays of the back reflection at an angle to the optical axis of the imaging optical unit. Accordingly, an imaging optical unit with an acceptance angle of 2.5° for example can detect optical rays of the back reflection that are reflected from the cornea to the imaging optical unit within a light cone with an opening angle of 5° with respect to the direction of incidence (i.e., with an opening angle of 2.5° between the lateral face of the light cone and the center line of the light cone), and so these rays can be collected by the imaging optical unit and can be used by the UVL-LVC system.

The disclosure offers the advantage that the back reflection of radiation radiated on the patient's eye by the imaging optical unit can be detected over a significantly larger angular range than what is possible using conventional UVL-LVC systems. Conventional UVL-LVC systems only have an acceptance angle of approximately 2° or less. In contrast to conventional UVL-LVC systems, the disclosure therefore enables the use of the back reflection for a relative centration of the UVL-LVC system in relation to the patient's eye since the back reflection can even be collected by the imaging optical unit and analyzed for centration purposes when the UVL-LVC system is not already in a centered position or in the direct vicinity thereof.

Consequently, the disclosure offers in particular the advantage that more reliable methods for automated centration and/or manual alignment which use the back reflection from the cornea can be carried out using a UVL-LVC system according to the disclosure.

As a result, the automated centration and alignment of the UVL-LVC system in relation to the patient's eye need not resort to the pupil center, which only renders a limited accuracy obtainable, but instead may consider other methods that use the back reflection, which have a greater accuracy and/or a higher reliability than a centration that makes use of the pupil center. Consequently, the reliability and accuracy of the centration, in particular of an automated centration, of the UVL-LVC system in relation to the patient's eye can be increased by the disclosure.

The UVL-LVC system according to the disclosure comprises a UV laser source which emits preferably pulsed laser radiation in the UV range. By way of example, this can be an excimer laser or a solid-state laser with wavelengths between approximately 193 nm and 213 nm. Moreover, the UVL-LVC system optionally comprises a scanning system for at least lateral scanning of the laser radiation in the x- and y-directions and preferably also for scanning in the z-direction, and an imaging optical unit for focusing (at least in terms of its lateral extent) the preferably pulsed laser radiation on the cornea of a patient's eye. This may lead to a photoablation process on the cornea, which represents, or is comprised by, the desired treatment. Optionally, the UV laser source is designed to emit pulsed laser radiation. Alternatively or in addition, the UV laser source is in the form of, or comprises, an excimer laser.

Optionally, the UVL-LVC system comprises a control unit for controlling all or some of the units of this system, for example the UV laser source, the scanning system and movable parts of the imaging optical unit. Moreover, the control unit may also serve to control movable parts, for example an application arm, and to position a contact interface. The control unit can be designed as a central control unit, or else be assembled from a plurality of partial units which are connected to one another. A specific planning unit for planning the operation may also be part of, or connected to, the control unit.

The imaging optical unit optionally comprises a microscope optical unit for focusing the preferably pulsed laser radiation on the cornea of a patient's eye, the optical opening of said optical unit being designed such that an acceptance angle for back reflections $\chi_{Max}$ detectable by the UVL-LVC system according to the disclosure of greater than 2.5°, optionally greater than 5°, optionally greater than 10°, optionally greater than 15°, optionally greater than 25° and optionally greater than or equal to 37° is obtainable. In this case, the imaging optical unit can be characterized in that the working distance is very small and the optical opening of the microscope optical unit is larger than in UVL-LVC systems according to the related art. As a result, back reflections from the cornea can be guided into the UVL-LVC system particularly effectively.

Optionally, the imaging optical unit has an optical opening and a given working distance such that a diameter of the optical opening is greater than or equal to the given working distance. This allows the provision of an imaging optical unit with a particularly large acceptance angle and, accordingly, a particularly large region in which the back reflection can be collected and used for centration purposes. Optionally, the imaging optical unit has an optical opening with a diameter of at least 50 mm, optionally at least 60 mm, and a working distance less than 50 mm and optionally less than or equal to 40 mm. Consequently, the working distance is significantly shorter than in the case of conventional UVL-LVC systems, as a result of which a significantly larger acceptance angle is obtainable than in conventional UVL-LVC systems.

The UVL-LVC system optionally comprises a contact interface for coupling the patient's eye to the UVL-LVC system. This may facilitate the stabilization of the patient's eye on the UVL-LVC system. Optionally, the UVL-LVC system further comprises a scanning system for laterally scanning the laser radiation in the x- and y-directions and optionally in the z-direction.

Optionally, the UVL-LVC system is designed to output couple the back reflection of the radiation detected by means of the imaging optical unit from the beam path of the laser radiation between the imaging optical unit and the scanning system. This offers the advantage of the back reflection not having to be guided over the scanning system, allowing possible losses accompanying this to be avoided. By way of example, a suitable sensor for detecting the output coupled back reflection may be arranged in the region between the imaging optical unit and the scanning system. Alternatively, the UVL-LVC can be designed to output couple the back reflection of the radiation detected by means of the imaging optical unit from the beam path of the laser radiation by means of the imaging optical unit. To this end, the imaging optical unit may for example comprise an appropriate output coupling optical unit. This may offer the advantage that the UVL-LVC may have a particularly compact form.

Optionally, the UVL-LVC comprises a detection system for returning beams formed by a detected back reflection of radiation radiated on the cornea of the patient's eye by the imaging optical unit and at least partially reflected by the cornea of the patient's eye, the returning beams optionally being formed by a centration beam.

In this case, a centration beam may be formed by an attenuated form of the laser beam provided for the treatment. In particular, the centration beam is embodied such that the latter does not have a treatment effect on the patient's eye but merely provides a back reflection from the cornea that is detectable by the UVL-LVC system. Alternatively or in addition, the centration beam may be provided in a different spectral range, for instance in the visible and/or infrared spectral range. To this end, the UVL-LVC system may comprise a further laser light source, for example. This offers the advantage of optionally being able to provide a centration beam which can be detected by conventional CCD and/or CMOS detectors and/or which is even visible to the human eye. Accordingly, the centration beam has, or consists of, a spectrum in the infrared and/or visible spectral range. Alternatively, the centration beam has, or consists of, a spectrum in the ultraviolet spectral range. Optionally, the latter is provided by an attenuated form of the laser radiation emitted by the UV laser source.

The UVL-LVC system optionally comprises a control unit, the control unit optionally being designed to carry out scan and position evaluation algorithms and/or algorithms for reflection analysis. This offers the option of an automated centration on the basis of the detected back reflection.

Optionally, the imaging optical unit is designed to provide a convergent focal field. Optionally, the imaging optical unit contains an objective for imaging the laser radiation in a focal field to this end, wherein the objective comprises a lens formed to provide the convergent focal field. The convergent focal field offers the advantage of being able to increase the homogeneity of the angles of incidence of the laser beam on the curved cornea and thereby likewise being able to increase the homogeneity of the fluence acting on the part of the cornea to be treated. As a result, a requirement for a fluence correction on the basis of the centration position of the UVL-LVC system relative to the cornea can optionally be dispensed with.

Optionally, the convergent focal field has a focal field diameter of at least 6 mm, optionally at least 8 mm and optionally at least 10 mm. This offers the advantage of the focal field diameter being of the same order of magnitude as the region of the cornea to be treated.

Optionally, each location in the convergent focal field has a local center of curvature on the side facing away from the focusing optical unit, and with each location in the focal field preferably having a focal field curvature with a radius $R_S$ ranging from 6 mm to 60 mm, optionally from 7 mm to 55 mm, optionally from 8 mm to 50 mm, optionally ranging from 10 mm to 30 mm and optionally ranging from 12 mm to 20 mm. This offers the advantage that the focal field curvature is similar in terms of magnitude to the curvature of the cornea and, accordingly, the fluence for the treatment of the cornea can be provided with a high degree of homogeneity.

Optionally, the imaging optical unit is designed to enable perpendicular impingement of a curved surface with the laser radiation, the curved surface having a local center of curvature on the side facing away from the imaging optical unit at each location, and wherein the curved surface has a diameter of at least 6 mm and/or a surface curvature with a radius $R_F$ ranging from 8 mm to 50 mm. This offers the advantage that the laser radiation is incident as perpendicularly as possible at each site of the region to be treated and, accordingly, a homogeneous fluence can be provided for a uniform treatment.

Optionally, the UVL-LVC system further comprises a distance determination unit which is designed to determine a distance between the imaging optical unit and the curved surface or the cornea of the patient's eye. This offers the option of radiating the curved focal field precisely on the cornea of the patient's eye, especially if the patient's eye has not been fixated by means of a contact interface or contact glass.

Optionally, the UVL-LVC system is designed to detect a Purkinje image in an angular range of at least 2.5° by detecting the back reflection of the radiation radiated on the cornea of the patient's eye by the imaging optical unit and at least partially reflected by the cornea of the patient's eye. This offers the advantage that the Purkinje image can be used over a broad angular range for the purposes of centering the UVL-LVC system relative to the patient's eye. As a result, it may be possible to dispense with the use of any other type of centration, for example on the basis of the pupil center. Optionally, the UVL-LVC system is designed to detect the first Purkinje Image In an angular range of at least 2.5°. Alternatively or in addition, one or more of the further Purkinje images can also be detected in an angular range of at least 2.5°.

Optionally, the UVL-LVC system is configured to use the detected Purkinje image for the fully automated centration and/or partially automated centration and/or manual alignment of the UVL-LVC system, with the automated centration and/or the manual alignment (possibly with the aid of a visualization of the back reflection for the user) optionally being implemented in accordance with the CSCLR condition. In this case, the UVL-LVC system can be designed to apply an algorithm for calculating a centration-corrected fluence loss function in the case of an automated centration by way of an allowance of the scan positions. This offers the advantage of enabling a particularly simple and reliable centration.

Optionally, the UVL-LVC system is configured to determine a detected position of the Purkinje image as an offset position, with the offset position characterizing a centration that deviates from the CSCLR condition. In this case, the UVL-LVC system can for example make an allowance for the offset position by means of the scanning apparatus, in order to obtain a precise treatment even if centration was carried out in relation to an offset position that deviates from the CSCLR condition.

Optionally, radiating the centration beam on the cornea of the patient's eye by an imaging optical unit is implemented in such a way that the centration beam has a convergent focal field with a radius of curvature $R_S$. In this case, the determination of the positioning and/or orientation of the UVL-LVC system relative to the patient's eye optionally comprises an analysis of the detected back reflection, with the determination of the positioning and/or orientation of the UVL-LVC system relative to the patient's eye being implemented using the radius of curvature $R_S$ of the convergent focal field, a predetermined corneal radius of curvature $R_C$ of the patient's eye and an axial distance between the cornea and the imaging optical unit. Moreover, radiating in the centration beam comprises a lateral scanning of the centration beam in the x- and y-directions and optionally in the z-direction by means of a scanning system and a determination of associated settings of the scanning system.

Optionally, the centration beam has a parallel beam and the detection of the back reflection comprises a detection of the first Purkinje image of the parallel beam. This offers advantages in respect of the detection of the Purkinje image and an evaluation of the Purkinje image in comparison with the radiated-in beam.

The method optionally comprises a determination of an offset position on the basis of the detected Purkinje image, the offset position characterizing a centration that deviates from a CSCLR condition. In this case, the method may further comprise a determination of an allowance of the UVL-LVC system in relation to the offset position. Moreover, the method may optionally determine adjusted coordinates for laser radiation to be radiated in for the treatment of the patient's eye whilst taking the offset position and the deviation from a centration according to the CSCLR condition connected therewith into account. This offers the advantage that a precise treatment can be implemented even in the case of a centration that deviates from the CSCLR condition.

Optionally, the method may comprise continually monitoring the offset position by means of an eye tracker and optionally updating the offset position should there be a change in the offset position determined by the continual monitoring. In particular, the continual monitoring can also be implemented during the treatment in order to ensure the precision of the treatment at all times.

At best, conventional systems use the first Purkinje image of the fixation laser or centration laser for the patient fixation of the system on the visual axis of the patient's eye ("target"). Under patient fixation, the recommended CSCLR condition is met when the Purkinje image is located at the center of the system optical unit and the optical system axis and the visual axis are lie coaxially above one another. However, as a result of the optical geometry of conventional systems, which have a very small acceptance angle for the entrance of the reflection into the optical beam path, it is only possible to find the first Purkinje image once the Purkinje image is already situated on the optical system axis or the deviation therefrom is minimal. However, the Purkinje image cannot be used for the alignment of the system in conventional systems once there is even only a small deviation from a correct centration (for example a deviation greater than 0.2 mm) since the optical opening of the systems is so small that the Purkinje image cannot be detected even in the case of the small deviations. Therefore, relatively large deviations cannot be corrected by means of the Purkinje image in conventional systems since said Purkinje image cannot be detected by the system in the case of relatively large deviations of the Purkinje image from the optical axis of the system. This is made even more difficult in the case of less cooperative patients, e.g., with a fixation weakness, since the Purkinje image is possibly lost again in this case even if a patient fixation thereon has already taken place. Moreover, the "parallax error" of the surgical microscope, that is to say different directions for the reflection in the right and left observer eye as a result of the binocular arrangement, makes a correct alignment more difficult in conventional systems. There is no automatic centration in accordance with CSCLR by way of Purkinje images in conventional systems, and this is not possible thereby either as a result of the restrictions arising from the optical geometry of conventional systems.

Optionally, the UVL-LVC system further comprises a radiation source for providing a centration beam in the form of one or more circles to be radiated on the cornea of the patient's eye by the imaging optical unit and a control unit designed to detect and analyze the back reflection of the radiation radiated in in the form of the circle or circles. Optionally, the UVL-LVC system further comprises a scanning system, with the centration beam in the form of one or more circles being provided by means of a punctiform centration beam and a deflection movement by way of the scanning system. This offers the advantage that the circles can be used for centering the UVL-LVC system on the patient's eye.

In this case, the analysis of the back reflection of the circle or circles optionally comprises an analysis of a deviation of the shape of the back reflection from the shape of the circle or circles of the radiated-in radiation. This offers the advantage that a deviation from the centered position can be recognized on the basis of a deviating shape of the back reflection of the circles from the radiated-in circles and/or their arrangement relative to one another and/or their position relative to the optical axis. Optionally, the control unit is configured to determine a correspondence of a system axis of the UVL-LVC system with the keratometric axis of the patient's eye when the deviation of the shape of the back reflection from the shape of the circle or circles of the radiated-in radiation is minimal or equal to zero. In particular, the deviation may be present in the form of a deviation from a circular form toward an elliptic form, in the form of a deviation from an equidistant arrangement of the circles or ellipses and/or in the form of a deviation from a concentric arrangement of the circles or ellipses about a common center of symmetry. Optionally, the system axis of the UVL-LVC system in this case runs through the vertex of the patient's eye and coaxially with respect to the keratometric axis when the deviation of the shape of the circle or circles of the back reflection from the shape of the circle or circles of the radiated-in radiation is below a given threshold value or equal to zero. This offers the option of a simple and reliable centration of the UVL-LVC system in relation to the vertex of the patient's eye. Optionally, the plurality of circles have different diameters.

Optionally, the control unit is configured to carry out an algorithm for calculating a centration-corrected fluence loss function. This offers the advantage of using the centration information for a precise adjustment of the fluence settings in order to obtain a treatment result that is as exact as possible.

Optionally, the centration beam is radiated in in the form of one or more circles by means of a punctiform centration beam, with a deflection movement being provided by way of a scanning system. Moreover, the method optionally further comprises an analysis of the back reflection of the centration beam radiated in in the form of one or more circles, with a positioning and/or orientation of a system axis of the UVL-LVC system being determined relative to the patient's eye on the basis of a deviation of the shape of the one or more circles of the back reflection from the shape of the circle or circles of the radiated-in radiation and/or their arrangement with respect to one another and/or their position with respect to the optical axis and/or on the basis of a symmetry between the radiated-in circles and their back reflections.

In this case, there may optionally be a determination of a correspondence of the system axis of the UVL-LVC system with the keratometric axis of the patient's eye when the deviation of the shape of the back reflection from the shape of the circle or circles of the radiated-in radiation is below a given threshold value or equal to zero. Likewise, the method may optionally comprise a determination of a profile of the system axis of the UVL-LVC system through the vertex of the patient's eye when the deviation of the shape of the back reflection from the shape of the circle or circles of the radiated-in radiation is below a given threshold value or equal to zero.

Optionally, the method may further comprise an automated centration of the system axis of the UVL-LVC system on the vertex of the patient's eye or an automated centration of the system axis of the UVL-LVC system on a point of the patient's eye that deviates from the vertex and determination of the deviating point of the patient's eye as an offset position. Moreover, the method may comprise determining adjusted coordinates for laser radiation to be radiated in for the treatment of the patient's eye whilst taking the offset position and the deviation from a centration according to the CSCLR condition connected therewith into account.

The related art has disclosed the practice of carrying out a manual centration on the vertex, which generally represents the reference center for the topography (topographic measurements are generally carried out on the keratometric axis), by entering displacement coordinates. This is frequently used for topography-guided corrections, but also for standard spherocylindrical corrections even though the correct reference axis in this case may be the visual axis. The latter is possible since, in the case of normal eyes, the positions of the CV ("corneal vertex," that is to say the intersection point of the keratometric axis on the cornea under patient fixation) with the ophthalmic pole, that is to say the visual axis, are sufficiently close together. This in turn is due to the fact that the center of curvature of the cornea approximately coincides with the second image-side optical node of the eye (cf. Gullstrand, Liou-Brennan eye models). The user frequently displaces the treatment center manually purely on the basis of the visual comparison with a topography measurement. Or they enter displacement coordinates into the system, which are generally specified in relation to the pupil center (CSC) and, for example, are taken from a topography measurement. What is disadvantageous in both cases is that the pupil diameter during the topography measurement does not necessarily correspond to the pupil diameter under the laser on account of differences in lighting. The frequently arising displacement of the pupil center with the pupil size then leads to a non-optimal centration as the corneal vertex has not been determined correctly.

Exemplary embodiments of the disclosure moreover also offer the option of carrying out an automated centration on the vertex, which is not known from the related art and which is not possible either using conventional systems.

The features and embodiments specified above and explained below should not only be considered to be disclosed in the respective explicitly mentioned combinations in this case, but are also comprised by the disclosure in other technically advantageous combinations and exemplary embodiments.

Further details and advantages of the disclosure, and technical backgrounds, should now be explained in more detail on the basis of the following examples and exemplary embodiments with reference being made to the drawings.

The aforementioned features of the disclosure, which are explained in various exemplary embodiments, can be used not only in the combinations specified in an exemplary manner but also in other combinations or on their own, without departing from the scope of the present disclosure.

BRIEF DESCRIPTION OF THE DRAWINGS

I The disclosure will now be described with reference to the drawings wherein.

DESCRIPTION OF EXEMPLARY EMBODIMENTS

The same or similar elements in the various exemplary embodiments are denoted by the same reference signs in the following drawings for reasons of simplicity.

Figure 1:
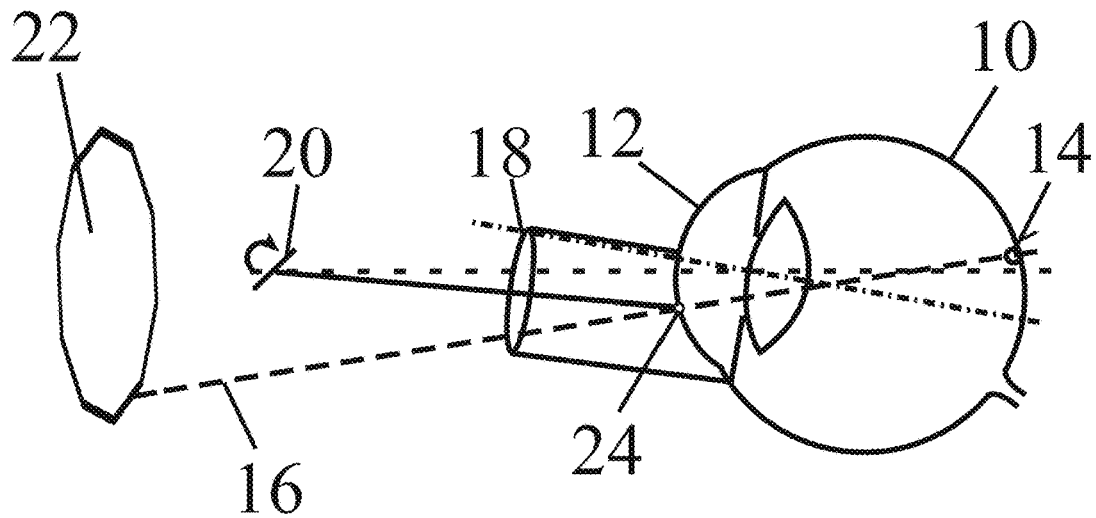
FIG. 1 shows a schematic representation of an unsuitably placed ablation profile.

FIG. 1 shows a schematic representation of the principle of how prismatic correction errors (tip/tilt) arise as a result of the insufficiently accurate use of an eye tracker according to a conventional centration method when the patient does not fixate on the center of the fixation object or the "fixation cloud." In this case, FIG. 1 depicts a patient's eye 10 with cornea 12 and fovea 14, and the optical axis 16 of the patient's eye or the visual axis 16, an ablation profile 18, a scanning system 20 and a fixation element 22, on which the patient should fixate with their gaze. The visual axis 16 intersects the cornea 12 at the ophthalmic pole 24.

If the patient does not fixate their eye 10 on the center of the fixation element 22 as envisaged but, for example, on an edge region of the fixation element 22, this may have as a consequence that the ablation profile 18 is not correctly applied along the necessary treatment axis (e.g., along the visual axis 16; defined by the ophthalmic pole (OP) and the point of the fixation element 22 fixated by the patient's eye 10 and hence not orthogonal to the visual axis 16). To provide a better overview, the relationships are depicted with much exaggeration in FIG. 1.

Therefore, avoiding the generation of such prismatic aberrations should be ensured when a patient's eye is treated using a UVL-LVC system. If this is not ensured, this may lead to the unwanted case of the ablation profiles 18 not being applied in the correct plane, that is to say not on the surface normal, i.e., perpendicular to the visual axis 16. This may be promoted by virtue of the patient preferably fixating in a largely fixed but "incorrect" direction, that is to say, e.g., permanently looking in a fixed direction that does not correspond to the center of the fixation element 22 (depending on refractive deficit and treatment duration, the patient can no longer see the fixation target in focus during the operation).

Figure 2:
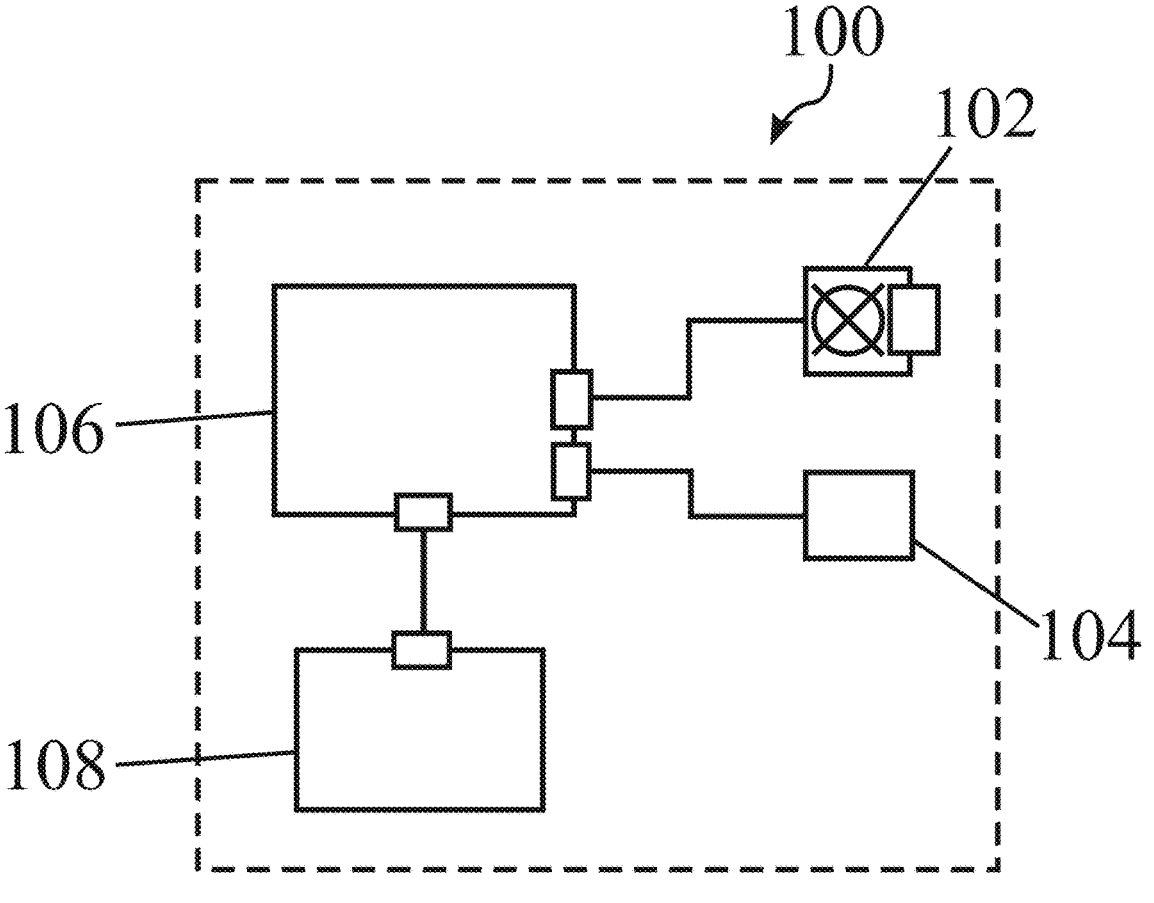
FIG. 2 shows a schematic representation of a UVL-LVC system according to an exemplary embodiment.

FIG. 2 shows a schematic representation of a UVL-LVC system 100 according to an exemplary embodiment of the disclosure. The UVL-LVC system 100 comprises a UV laser source 102, a scanning system 104, a control unit 106 and a planning unit 108. For data exchange between the control unit 106 and the UV laser source 102, the scanner 104 and the planning unit P, the control unit 106 has interfaces (represented by boxes on the control unit S), by means of which the data line can be transferred by way of cables. The planning unit 108 likewise comprises an interface (depicted as a box on the planning unit P) for data exchange with the control unit 106. A wireless transfer is likewise possible. The planning unit 108 has a computing unit (not depicted), by means of which the planning data are calculated. The terms scanner and scanning system are used synonymously in this description.

Figure 3A:
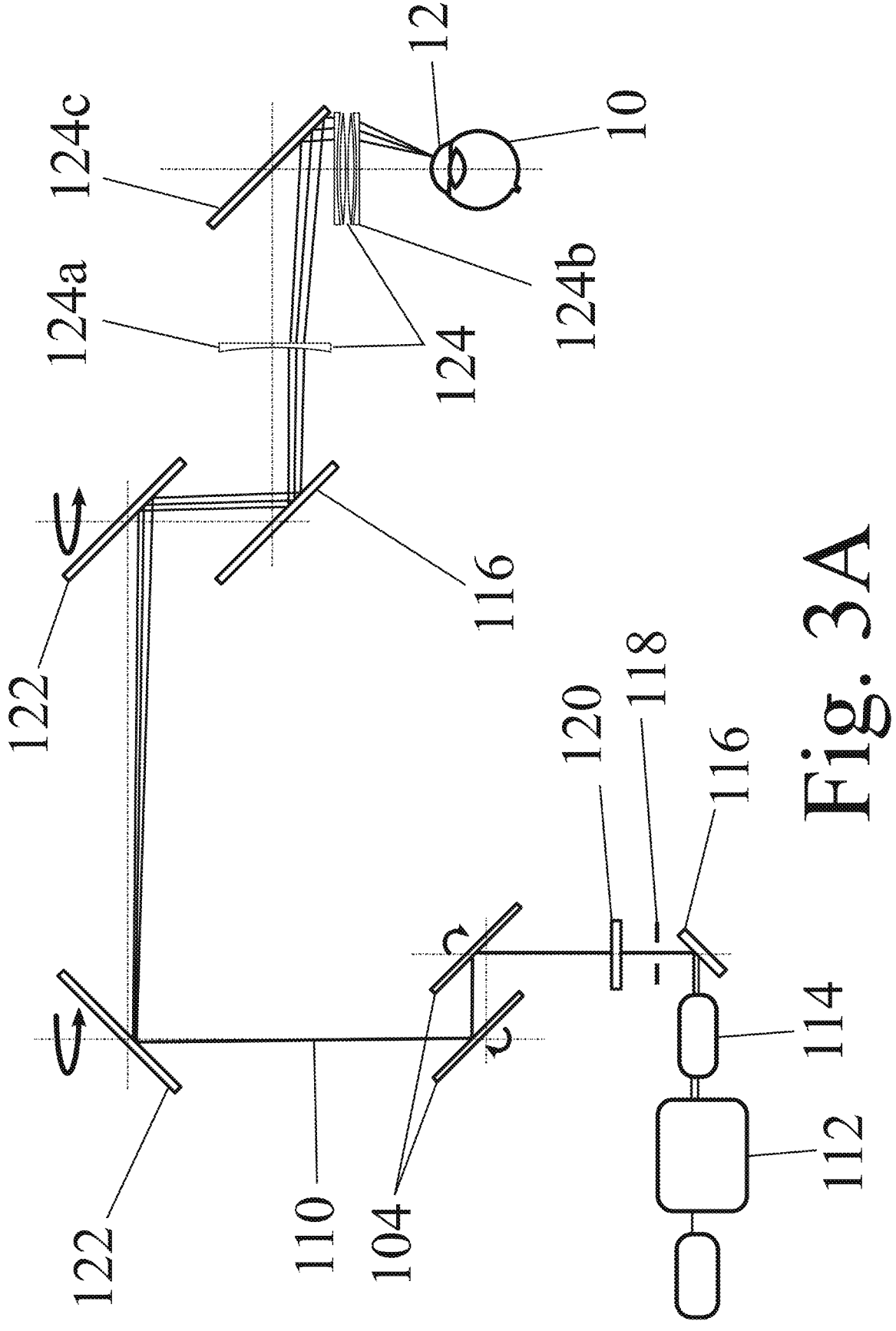
FIG. 3A shows a beam profile of a UVL-LVC system according to an optional embodiment.

FIG. 3A shows a basic arrangement of the optical beam path of an exemplary embodiment of a UVL-LVC system 100, in particular of the use part of the UVL-LVC system 100, in an exemplary fashion. A laser beam 110 is provided by an excimer laser 112 as a UV laser source. The laser beam 110 is attenuated by an (optional) optical attenuator 114, deflected by a deflector 116, is incident on a stop (or a pinhole) 118 and subsequently reaches the beam shaper 120. The latter serves to shape the beam of the raw excimer laser beam into a Gaussian or supergaussian pulse fluence distribution. By way of the scanning system 104, the laser beam 110 can be deflected laterally in the x- and y-directions (depicted by way of bent arrows). From here, the laser beam 110 is guided in a first articulated arm.

In the exemplary embodiment shown, the latter is movably connected to a base unit (not plotted) by way of a first rotary joint 122 (symbolized by an axis of rotation and a rotation arrow). The base unit comprises the laser source 102 or the excimer laser 112, the optical attenuator 114, the stop 118 (and the deflector 116 which is situated in the beam path between the optical attenuator 114 and the stop 118), the beam shaper 120 and the scanning system 104. The first articulated arm is movably connected to a second articulated arm by way of a second rotary joint 122 (symbolized by an axis of rotation and a rotation arrow) on the side distant from the base unit. Optionally, one or more further rotary joints may be formed (not shown). The laser beam 110 is guided into the second articulated arm via two further deflectors 116 by way of the second rotary joint 112. From there, the laser beam 110 is steered in the direction of the patient's eye 10 by way of a further deflector 116. In this case, the laser beam 110 is focused on the cornea 12 of the patient's eye 10 by way of a focusing optical unit or imaging optical unit 124. In this case, the imaging optical unit 124 has a two-part structure. A deflector 124*c* is situated in the beam path between the first lens group 124*a* and the second lens group 124*b*. The required lenses of the two lens groups 124*a*, 124*b* are only depicted correctly in a schematic sense. In this case, the imaging optical unit 124 is embodied so that the latter has an acceptance angle of at least 2.5° for detecting a back reflection of radiation radiated on the cornea by the imaging optical unit.

Figure 3B:
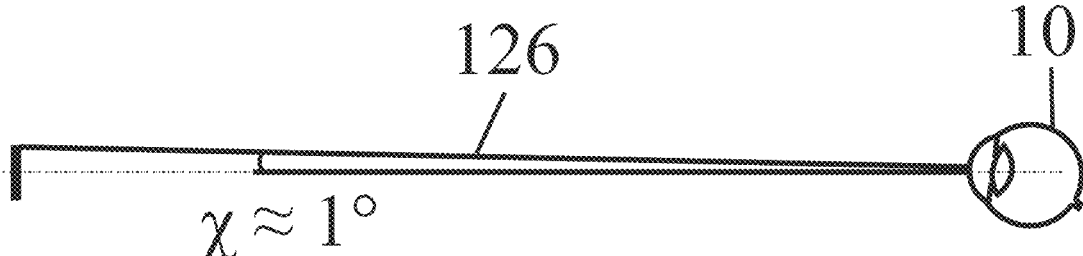
FIG. 3B shows an exemplary acceptance angle of a conventional UVL-LVC system.
Figure 3C:
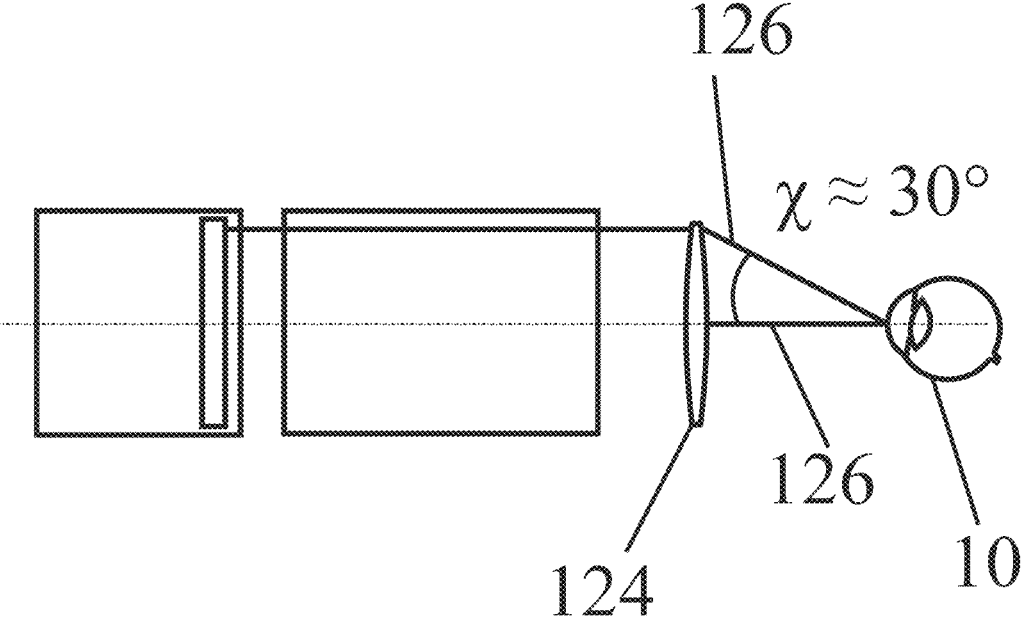
FIG. 3C shows an exemplary acceptance angle of a UVL-LVC system according to an exemplary embodiment.

In schematic representations, FIGS. 3B and 3C elucidate a conventional UVL-LVC system (FIG. 3B) with an acceptance angle for back reflections 126 of approximately 1° in comparison with a UVL-LVC system according to an exemplary embodiment of the disclosure with an acceptance angle of approximately 30°.

For example, methods according to exemplary embodiments of the disclosure are described below, which methods can be carried out, for example, using a UVL-LVC system as described with reference to the figures above.

Radiating radiation, in particular a laser beam for treating the patient's eye 10 and/or a centration beam, on the cornea 12 by the imaging optical unit 124 produces a back reflection since at least some of the radiated-in radiation is reflected by the cornea 10. In this case, the back reflection is cast back in the direction of the UVL-LVC system and detected by the imaging optical unit on account of the large acceptance angle. The decentration of the UVL-LVC system according to the disclosure with respect to the corneal vertex can be determined using a suitable sensor system from the position of the back reflection and with the knowledge of the geometry of the arrangement, the corneal curvature (K-values)

and the optical imaging. Thus, it is possible to determine the 1st order Purkinje image and, by way of the allowance of the scanning system 104, center the UVL-LVC system 100, for example toward the visual axis 16. Thus, various options of autocentration arise for the UVL-LVC system 100 according to the disclosure, for example on the vertex or on an offset position deviating from the vertex, and a precise coaxial alignment between visual axis 16 and system axis appears not to be required. As a result of the scanner allowance in conjunction with the imaging optical unit, which may be in the form of, or comprise, a microscope optical unit, the system is able to realize the centration according to the CSCLR condition. In this case, the centration procedure requires a fixation of the patient on the fixation target.

A UVL-LVC system 100 according to an exemplary embodiment uses the Purkinje image for the centration in this case. As a result, the imaging optical unit 124 at the exit aperture and the large acceptance angle enable the detection of the back reflection and this allows the reflection belonging to the CSCLR to be found by means of the Purkinje image.

Figure 4:
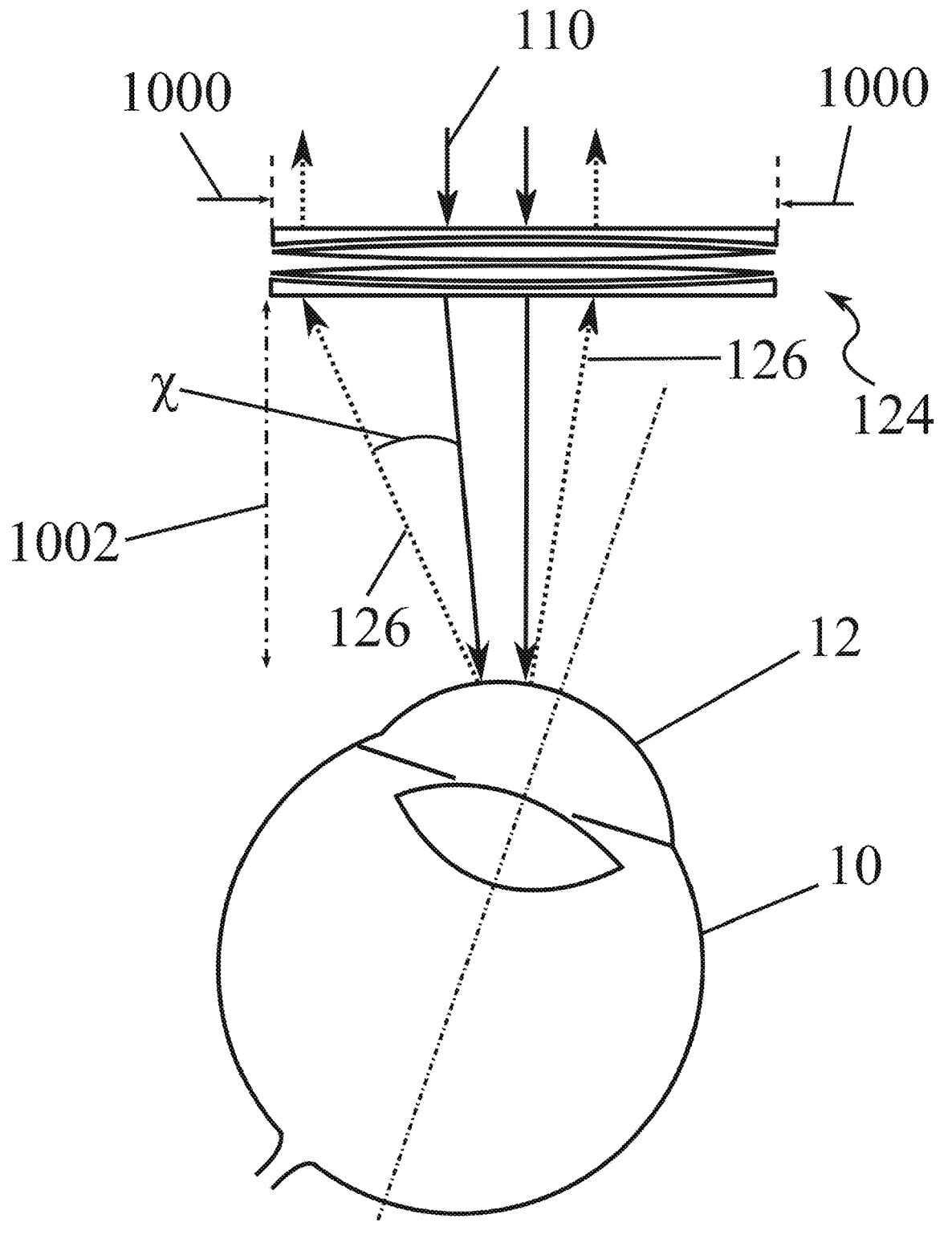
FIG. 4 shows an exemplary representation of a patient's eye with a centered imaging optical unit of a UVL-LVC system.

This is illustrated in FIG. 4 in exemplary fashion. It shows a schematic representation of a patient's eye 10 with a centered imaging optical unit 124 of a UVL-LVC system 100. It is evident here that the optical opening 1000 of the imaging optical unit is approximately of the same order of magnitude as the working distance 1002 to the cornea 12 of the eye. Accordingly, the imaging optical unit has a large acceptance angle, approximately 37° in the exemplary embodiment shown, for collecting a back reflection from the cornea 12. It should be observed that the UVL-LVC system in FIG. 4 is not depicted as centered in relation to the keratometric axis (connecting line between vertex and fixation target under patient fixation). FIG. 4 further shows, in exemplary fashion, a laser beam 110 (solid line) radiated onto the cornea 10 by the imaging optical unit 124 and the back reflection 126 (dashed line) reflected by the cornea 10, said back reflection being reflected back to the UVL-LVC system with an opening angle $\chi$ and being collected by the imaging optical unit 124.

The advantageous imaging optical unit of the UVL-LVC system 100 is accompanied here by an optimization and significant simplification of the manual method of UVL-LVC systems according to the related art and additionally enables an automated centration using the Purkinje image. To this end, the UVL-LVC system according to the disclosure detects and visualizes the Purkinje image which returns into the system in the case of a certain eye position. On account of the large acceptance angle, it is visible even in the case of relatively large displacements of the eye from the CSCLR condition. In the case of a manual centration, the user displaces the use part only until the visualized reflection enters the center of the system optical unit, as a result of which the CSCLR condition (coaxial alignment) is satisfied.

Moreover, in the case of symmetry between the scanning beam direction and the reflection direction in relation to a parallel to the optical system axis, the UVL-LVC system 100 is able to determine a corneal point whose normal is parallel to the optical axis. To this end, the scanning beam must be varied by the system. As a result, the treatment center can be automatically displaced to this point by way of appropriate scanner offset coordinates (automatic centration by way of a scanner allowance). Thus, the user no longer needs to displace the use part manually in order to bring the Purkinje image into the optical center (or the system can optimize a non-optimal manual centration by the user); instead, the same is displaced to the associated coordinate ("virtual CSCLR centration").

Moreover, the corneal coordinate belonging to the found CSCLR or virtual CSCLR is optionally referenced in the UVL-LVC system 100 to the simultaneously detected pupil and/or iris and/or limbus. This means that the back reflection detection is no longer required once the corneal coordinate belonging to the CSCLR (also applies to the vertex position) has been found and referenced once. Hence, even a moderate slippage during the docking process of a contact interface used in the UVL-LVC system according to the disclosure can be compensated, or a reliable automatic re-centration in the case of a contact interface detachment ("suction loss") is possible after the interface has been reapplied.

A further exemplary embodiment of the disclosure is described in exemplary fashion below on the basis of the Purkinje image. On the one hand, the principles of solving the Purkinje image determination were already described above, see FIG. 4; further backgrounds are explained below.

In principle, there is not just one Purkinje image. A reflection always occurs when the cornea is irradiated and, in the case of the 1st order Purkinje image, this reflection is naturally determined by the law of reflection at the anterior corneal surface. In ophthalmology, the Purkinje image frequently means the reflection corresponding to the Purkinje image under CSCLR conditions. In principle, this is due to the fact that this reflection is only seen in conventional UVL-LVC systems according to the related art when the patient is (almost) correctly positioned in any case; this is sometimes referred to as "Purkinje image centration."

A difference radius of curvature $R_A$ relevant to a precise treatment is explained with reference to FIG. 5. In this case, the difference radius of curvature $R_A$ is formed from the difference between the focal field radius of curvature $R_S$ (scanning radius of curvature) and the corneal radius of curvature $R_C$. In this case, the calculation is a good approximation on the basis of a spherical functionality (sphere model) for the cornea or the focal field.

Figures 5, 6:
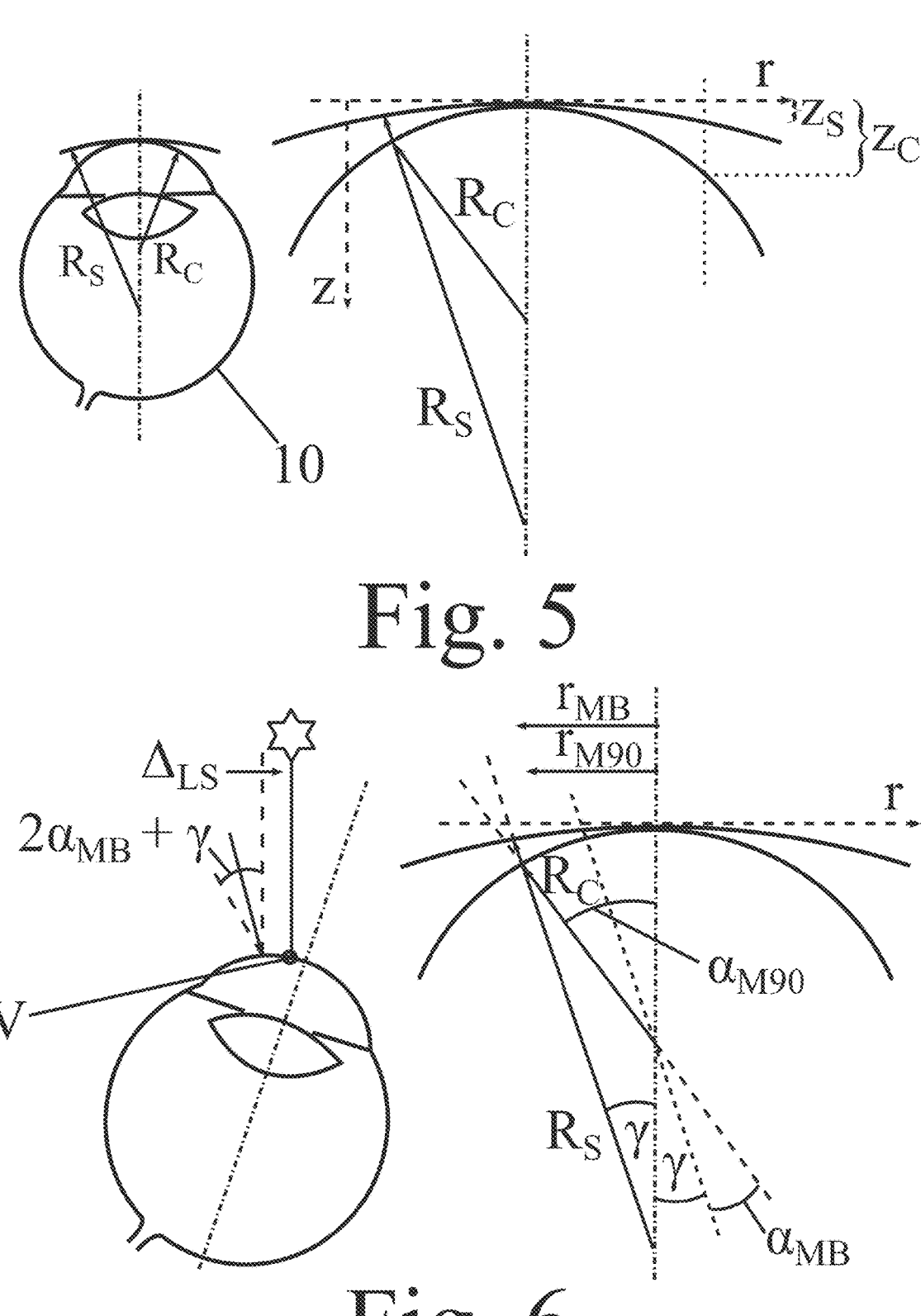
FIG. 5 shows an explanation for the difference radius of curvature $R_A$.
FIG. 6 shows an explanation for the principle of the non-coaxial alignment of a patient during fixation.

In this case, FIG. 5 shows, on the left, a schematic representation of a patient's eye 10, in which the focal field radius of curvature $R_S$ and the corneal radius of curvature $R_C$ are depicted. On the right, a magnified representation of the radii of curvature with the coordinate system of the spherical function is shown.

In this case, the coordinate z depends on the radial variable r and the radius of curvature R (formula 1). This yields a mathematical description of the difference radius of curvature $R_A$ (formulas 2 to 4):

$$z(R,\ r) = \frac{r^2}{R + \sqrt{R^2 - r^2}} \tag{1}$$

$$\Delta z(R_C, R_S, r) = z_C(R_C, r) - z_S(R_S, r) = z(R_A, r) \tag{2}$$

$$\frac{1}{R_A + \sqrt{R_A^2 - r^2}} = \frac{1}{R_C + \sqrt{R_c^2 - r^2}} - \frac{1}{R_S + \sqrt{R_S^2 - r^2}} \tag{3}$$

$$\rightarrow (r = 0): \frac{1}{R_A} = \frac{1}{R_C} - \frac{1}{R_S} \tag{4}$$

$$\rightarrow R_A = \frac{R_c R_S}{R_S - R_c} \tag{5}$$

According to an exemplary embodiment, it is advantageous if the UVL-LVC system is designed such that the focal field radius of curvature $R_S$ is of the order of magnitude of typical corneas. In particular, it may be advantageous for the imaging optical unit to be embodied accordingly. This offers the advantage of being able to achieve a significant reduction in the fluence losses. The calculation explained with reference to FIG. 5 determines the difference radius of curvature $R_A$. This corresponds to an "effective" corneal curvature for light incident from the z-direction. Expressed differently, the difference calculation—figuratively speaking—fictitiously bends the cornea by the focal field radius of curvature. Consequently, with a typical corneal radius of curvature of $R_C$=7.86 mm, values of approximately $R_A \approx 450$ mm to approximately $R_A \approx 15$ mm arise for the effective corneal curvature for focal field radii of curvature with values between approximately 8 mm and approximately 16 mm. Determined as a result of the law of reflection, these parameters influence the direction of the rays reflected by the cornea. By way of example, if the reflections of the radiated-in pulsed laser beam themselves are intended to be used for the back reflection detection (see below), it is immediately obvious how the reflection angle depends on the irradiation direction and the corneal normal at the point of reflection on the cornea (which is the same as the irradiated location), which also depends on the displacement of the eye under the application part.

A special feature of the imaging optical unit in conjunction with the remaining system optical unit of the UVL-LVC system is that, thanks to using the same optical unit for the laser beam feed to the eye, light cast back by the cornea (e.g., Purkinje image) can be effectively "collected" by the system and, when necessary, can be guided back to the base unit in the optical system. In particular, this can be simplified by virtue of integrating the scanning system at the start of the beam path (from the point of view of the UV laser source). Then, the light collected from the eye can be deflected or decoupled at suitable sites in the beam path of the optical unit and, for example, be supplied to detectors before it reaches the scanning system. In this case, the acceptance angle for collecting the light cast back from the cornea in the microscope objective is optionally particularly large and the imaging has been particularly optimized to this end in the remaining system optical unit.

An approximate determination of the reflection angle in a UVL-LVC system according to an exemplary embodiment is explained on the basis of FIG. 6. On the left, FIG. 6 represents a non-coaxial fixation of the patient's eye (dashed line) in comparison with a coaxial fixation according to the CSCLR condition at the vertex (solid line). Attention is drawn to the fact that the representation is simplified, especially in relation to the corneal shape. In this case, the indices "MB" denote statements regarding a system according to an exemplary embodiment of the disclosure and the indices "M90" denote statements regarding an exemplary, conventional system according to the related art. An estimate of the angle of incidence of the beam on the cornea $\alpha_{MB}$ in the UVL-LVC system depending on the pupil coordinate $r_{MB} \approx r_{M90}$ is depicted on the right. The lateral displacement $\Delta_{LS}$ then yields the reflection angle $2\alpha_{MB}+\gamma$. In this case, the angle $\gamma$ is the angle between the system axis and the radial vector $R_S$ of the focal field, which points to the location of incidence of the laser radiation (see FIG. 6, right hand partial image). In this case, $\Delta_{LS}$ is used in the calculation for the pupil coordinate $r_{M90}$. The ophthalmic pole (OP) and the corneal vertex (CV; also referred to as Vertex) are equated here without loss of generality. The following applies to the angles $\gamma$ and $\alpha_{MB}$:

$$\gamma = \sin^{-1}\left(\frac{r_{MB}}{R_S}\right) \approx \sin^{-1}\left(\frac{r_{M90}}{R_S}\right) \tag{6}$$

$$\alpha_{M90} = \sin^{-1}\left(\frac{r_{M90}}{R_C}\right) \tag{7}$$

Suitable conditions for detecting a beam reflected from the cornea also arise for the application using the aforementioned values for the focal field radius of curvature $R_S$. To demonstrate this, the left-hand side of FIG. 6 shows the principle of the non-coaxial alignment of a patient during fixation. Although the target is fixated (attention is drawn to the fact that a directed laser beam is used as a target (green)), the patient is not aligned coaxially with the optical system as would correspond to the correct centration according to the CSCLR condition (solid line). A displacement of the system axis (optical axis) of the UVL-LVC system of $\Delta_{LS}$=2 mm in relation to the CSCLR condition (i.e., a displacement of the dashed beam path in relation to the solid beam path, in the case of the scanning system in the zero position) and a focal field radius of curvature $R_S$ of 12 mm are assumed. The dashed beam arises by way of a suitable beam guided through the scanning system, e.g., the alignment beam, in the case of the zero position of the scanners. The calculation of the reflection angle $2\alpha_{MB}+\gamma$ with the formulas of the right-hand side of FIG. 6 and $r_{M90}=\Delta_{LS}$ then yields a reflection angle of approximately $2\alpha_{MB}+\gamma$=20°. This angle is detected without problems by the imaging optical unit and can be processed in the UVL-LVC system.

The system structure with the imaging optical unit is advantageous in conjunction with the remaining system optical unit because the light cast back by the cornea can effectively be "collected," detected and processed by the system.

The focal field radius of curvature $R_S$ and the corneal radius of curvature $R_C$ were only equated for the better understanding of the following explanations. The precise optical beam path from the imaging optical unit (from the point of view of the beam source) plays no role in the following considerations.

The patient is fixating but the CSCLR condition has not been met (cf. $\Delta_{LS}$ in FIG. 6 and descriptions). Different paths arise for incoming and reflected beams when scanning over the eye using a suitable beam that is deflected by the scanners (FIG. 7).

Figure 7:
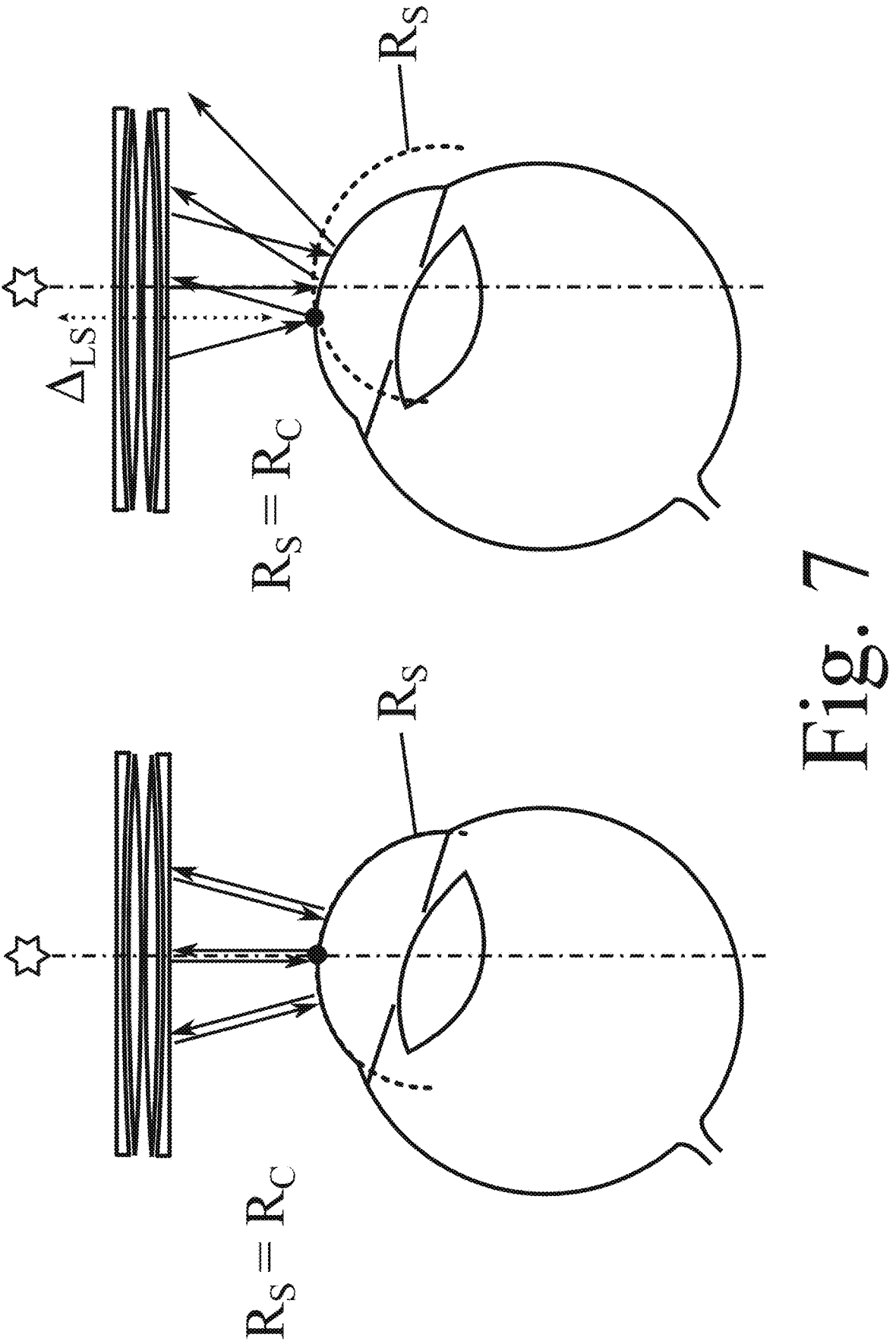
FIG. 7 shows an explanation for the principle of a Purkinje image finder.

FIG. 7 is used to explain the principle of the Purkinje image finder (or ophthalmic pole finder), i.e., a method for centering the UVL-LVC system on the basis of the Purkinje effect according to an exemplary embodiment. To this end, the assumption is made that the focal field radius of curvature and the corneal radius of curvature are equal, that is to say $R_S=R_C$. The CSCLR condition has been satisfied in the left-hand image, but not in the right-hand image. The patient's eye is fixated but displaced to the left in relation to the system axis of the UVL-LVC system (see vertex). The focal field radius of curvature is represented by a semicircle 1004 in each case (dotted on the right). The dotted double-headed arrow 1006 in the right partial figure indicates that the incoming beam would be reflected back on itself if there could be telecentric irradiation.

Under the CSCLR condition (left-hand partial image), the beams are cast back onto themselves in the case of reflection, with $R_S=R_C$ applying. Should this not be the case, there nevertheless is a symmetric profile of the deviations about the system axis (that is to say when scanning to the left or right in the image) which can be calculated from the difference between $R_S$ and $R_C$ (and this may also be calculated in the case of aspherical or ellipsotoric corneas). The CSCLR reflection, or the ophthalmic pole belonging to this axis, typically occurs very close to the corneal vertex CV. In medical practice, the Purkinje image of the CSCLR condition consequently frequently determines the vertex, and vice versa.

Should the CSCLR condition no longer be satisfied, the beams will no longer be reflected back onto themselves ($R_S$=$R_C$) or a beam profile will no longer be symmetric ($R_S$ not equal to $R_C$), and a beam profile as shown in the right partial image occurs instead. It is only true for the scanning direction which leads to the corneal point (the ophthalmic pole) belonging to the CSCLR (in practical terms the vertex) that the reflected beam is reflected back symmetrically ("symmetric beam pair") in relation to the displaced axis (see $\Delta_{LS}$) ("quasi" CSCLR condition). All other beams exhibit an increasing deviation of the reflections to the right, that is to say in the same direction.

Manual Positioning and Automated Centration by Way of Alignment:

In the case of the manual centration, the user displaces the imaging optical unit (or the use part with the integrated optical unit) laterally over the eye in the xy-plane (use part) until the corneal reflection (Purkinje image) of the central centration beam coming in along the optical system axis travels back centrally into the system (i.e., coaxially with respect to the system axis). Then, the CSCLR condition would be satisfied under patient fixation and the visual axis and system axis would be coaxial. An automated system-controlled displacement (xy-displacement) would achieve the same.

A suitable visualization for the user is required for both methods. By way of example, this could be/shown as an auxiliary circle and a "vector image" of the reflection as a superposition for eye visualization. A wide variety of suitable representation options are conceivable, right down to a pure numerical display of suitable numerical values. Moreover, the measuring procedure must be permanently repeated during the manual positioning and, advantageously, also during the automated centration by alignment and the representation must be updated accordingly with a certain repetition rate.

The centration attained thus is advantageously also referenced in relation to the simultaneously detected pupil and/or iris and/or limbus (i.e., the eye position in relation to the system is determined, "reference position") in order to be able to compensate possible slippage of the contact interface during the docking process or in order to be able to enable a reliable re-centration (e.g., in the case of "suction loss"), which is possible with the aid of the reference position. A possibly implemented eye tracker system would preferably be used for registration purposes in the case of solutions without the contact interface.

By way of example, the fixation laser which runs coaxially with the system optical unit can be used as incoming scanning beam in the case of the manual centration and in the case of the automated centration by alignment. Alternatively, use can be made of a suitable beam guided over the scanners, e.g., the alignment beam, in the case of the zero position of the scanners. Other separate, preferably monochromatic beam sources are likewise conceivable. Thus, even the pulsed laser beam could be used in the case of a suitable attenuation (see also below). The scanning beam direction is calculable in the case of the known dispersion of the optical units and the imaging geometry. The directions of therapy beam and scanning beam run identically if the scanning beam has the same wavelength as the therapy beam (UV).

Automated Centration by Way of Scanner Allowance

The known geometry of the optical imaging in the UVL-LVC system according to the exemplary embodiment and knowledge of $R_S$ and $R_C$ can be used to determine the "symmetric beam pair" (i.e., also the position of the detected back reflection) and the associated scanning position ("offset position"), which also determines the position of the corneal point belonging to the "symmetric beam pair." This provides the "offset position" of the corneal point virtually belonging to the CSCLR condition (ophthalmic pole for the centration of the ablation on the cornea according to the CSCLR condition) in relation to the optical axis of the system.

This allows an automated centration, which may be realized by the scanner with an allowance in relation to the offset position.

In practice, the situation is made more difficult during this automated procedure by the fact that, as a rule, the focal field radius of curvature $R_S$ and the corneal radius of curvature $R_C$ are not equal. The effective radius of curvature can be determined in turn if the corneal radius of curvature $R_C$ of the patient (or the keratometric k-values (or the associated principal curvature radii) of the cornea in the case of ellipsotoric corneas) and the focal field radius of curvature $R_S$ are known. Using this value and the geometry data (of the optical imaging in the UVL-LVC system according to the disclosure), it is possible to calculate the angle of reflection that fits to the quasi CSCLR condition under patient fixation. Precisely this angle can be found by scanning the cornea.

The found Purkinje image belonging to the CSCLR condition or the associated scanner position ("offset position") can now be used to convert the scanning coordinates for the ablation pulses such that these are adapted to the individual case for the ablation of the eye under a contact interface, especially even if the system is not positioned coaxially with respect to the CSCLR condition.

Naturally, this is a 2-dimensional problem and also requires a 2-dimensional scan and appropriate analysis. For an automated centration, the "offset position" for all pulse coordinates is used to displace the treatment center during the ablation to the corneal coordinate belonging to the CSCLR condition. Thus, the user need not align the Purkinje image by manual displacement of the use part.

It should be observed that there should be a correction of the fluence loss compensation function by the UVL-LVC system in this case. This can be implemented with knowledge of the optical geometry, $R_S$, $R_C$ (or the keratometric data of the cornea; see above) and the determined "offset position."

However, this is only conditionally possible without thwarting the advantages by way of an improved fluence loss compensation. Other limiting aspects in respect of the autocentration also need to be considered so that the accuracy of the ablation is not compromised. The eye must thus have already been positioned "relatively" well, that is to say "near the CSCLR criterion."

The "offset position" is advantageously also referenced in relation to the simultaneously detected pupil in order to compensate a possible slippage of the contact interface during the docking process or to enable a reliable re-centration (e.g., in the case of "suction loss").

In a further exemplary embodiment, the offset position is detected simultaneously by way of a tracking signal of an eye tracking system. In this case, the eye tracker continually detects the position of the pupil with a high repetition rate.

Preferably, the eye tracker moreover detects the limbus position and/or the iris in this case. Moreover, the current tracking position of an eye tracker is evaluated at the instant of determining the offset position by way of the methods presented above.

In the case of eye movements that occur during the treatment in the case of an eye that has not been docked by means of the contact interface, this offset position can then be continuously updated by way of the output signal of the eye tracking system. Hence, the correct centration of the treatment can be maintained, at least for small eye movements, in the case of eyes that cannot be docked, for example for medical or anatomical reasons. The only disadvantage is that a continual recalculation of a fluence loss compensation with the cycle of the eye tracking data currently still is too complicated, and this advantage of a docked eye cannot be fully maintained.

The implementation of the procedure requires a suitable, preferably monochromatic centration beam for the scan. By way of example, an input coupled laser, or else the alignment beam laser, can be used to this end. The latter passes through the scanners and is therefore particularly suitable. Thus, there is also no need to install additional scanners; the scanners for the deflection of the ablation laser beam can be used instead. For a sufficient accuracy, it is advantageous if the focus of the incoming centration beam is of the order of approximately 0.5 mm or less as a result of the optical unit. The exact wavelength for which the microscope optical unit has been designed needs to be taken into account here.

Preferably, the centration beam is designed such that it is incident on a detector in focus following reflection on the eye (which corresponds to the effect upon passage through a divergent lens on account of the curvature) and passage through the focusing optical unit of the therapy beam and the detection optical unit of the reflection light.

Furthermore, fast and intelligent scanning methods are advantageous. There is no need to use a static scan. Rather, it is possible to implement effective and fast scanning algorithms on the basis of the problem geometry (e.g., extended Newton methods, etc.). Moreover, the solution requires fast position evaluation algorithms and detection systems such as, e.g., cameras etc. By way of example, deflectors or beam splitters can be used for imaging the incoming and/or leaving beams onto the detection systems. Software for visualizing user assistance functions, for example direction or proximity indicators for the manual centration, is furthermore advantageous, as is an algorithm for calculating the "centration-corrected fluence loss function."

For the sake of completion, attention is drawn to the fact that the reflection detection method can be used both pre-operatively and during the treatment, within the scope of scattering on the rough, treated (i.e., ablated) stromal surface. This is usable as an online topography method and for ablation monitoring. To this end, accurate knowledge of the distance between cornea and focusing optical unit is advantageous; it may also be determined optically by way of suitable measuring means, for example OCT, strip projection or sensor systems based on the spectral processing of reflections in optical units with longitudinal chromatic aberrations.

In a special configuration, the ablation laser beam itself (as an "incoming beam") can be used during the ablation for the Purkinje image detection.

Such an application of the ablation beam as a Purkinje image signal prior to the actual ablation is also conceivable, provided this is carried out using a significantly attenuated treatment beam.

To this end, and optionally also for other exemplary embodiments, the attenuation of not only the UV laser energy below the threshold compatible with laser safety is preferably advantageous, but preferably also a spatial filtering of the UV light, which may have a large spatial extent in the relevant part of the beam path, as said large spatial extent otherwise is counter to a high spatial resolution upon detection.

According to an exemplary embodiment of the disclosure using the Purkinje image, the following three options are consequently available for centration:

Manual positioning/centration, for example by way of a graphical output of an image representation of the Purkinje image for the user Automated centration by the system on the basis of the CSCLR condition Automated centration by an allowance of the scanner system at an offset point away from the CSCLR condition.

The first two variants have different types of implementation. Thus, only the imaging optical unit may be displaced according to an exemplary embodiment. Alternatively, the entire internal optical unit may be displaced together with the imaging optical unit, which is advantageous to the effect of the optical system axis also being displaced. By way of example, this can be achieved by displacing the use part (with the optical axis of the system then automatically removed as well, that is to say also being displaced therewith) and/or by virtue of a xy-displacement unit displacing the complete optical beam guidance of the laser system.

In the case of the manual positioning/centration, the user for example displaces the use part or the imaging optical unit above the patient's eye until the (visualized) reflection is at the center of the system optical unit, as a result of which the CSCLR condition (coaxial alignment) is satisfied.

Using suitable software (analysis of the back reflection direction from the detected reflection position on a suitable detector) and hardware (xy-displacement unit for the application part or (parts) of the laser system), it is also possible for the system to carry out the alignment automatically (automated centration by alignment). To this end, the back reflection is preferably detected in the case of the optical axis of the system being irradiated centrally (as a result of which the reflection direction is also known from the geometry of the arrangement). Optionally, a control signal for the displacement of the xy-displacement unit can be derived from the deviation of the direction of the reflection from the scanning beam. The system then displaces the application part or the microscope optical unit (directly or via (parts of) the laser system) in a direction which renders the reflection coaxial with respect to the central scanning beam, as a result of which the CSCLR condition is then attained. This will preferably be implemented in control loops during which the system continually undertakes the reflection detection and the displacement of the application part with a suitable repetition rate, until the perfect alignment of the eye with respect to the application part has been obtained.

Moreover, in the case of symmetry between the scanning beam direction and the reflection direction in relation to a parallel to the optical system axis, a UVL-LVC system according to an exemplary embodiment is able to determine a corneal point whose normal is parallel to the optical axis. To this end, the scanning beam or centration beam must be varied by the system. The point on the cornea belonging to the (quasi, see above) CSCLR condition or to the quasi CSCLR condition can be determined by an analysis of the back reflections. As a result, the treatment center can likewise be fully automatically displaced to this point by way of appropriate scanner offset coordinates (automatic centration by way of an allowance of the scanner system). Thus, the user no longer needs to displace the use part manually in order to bring the Purkinje image into the optical center (or the system can optimize a non-optimal manual centration by the user); instead, the same is displaced to the associated coordinate ("virtual CSCLR centration").

Further exemplary embodiments of UVL-LVC systems according to the disclosure and methods which consider a centration of the UVL-LVC system on the vertex are explained below. In this case, a manual method by entering a displacement coordinate and an automated centration option in relation to the vertex, in particular, represent such exemplary embodiments.

In this case, there are three methods analogous to the CSCLR condition:

1. Manual positioning
2. Automated centration by alignment
3. Automated centration by way of scanner allowance In this case, a plurality of rings arranged at the same distance from, and concentrically with respect to, one another are radiated on the cornea by the imaging optical unit and the back reflection from the cornea is detected by means of the imaging optical unit within an angular range of at least 2.5°. According to option 1, the user moves the use part such that the back reflection of the rings radiated-in by the imaging optical unit is as circular and as symmetrical as possible (same ring spacings in all directions) and centered with respect to the optical axis. Moreover, the ring patterns are displaced in the direction of the optical system axis. In the case of a decentration of the system axis with respect to the vertex (more precisely, with respect to the keratometry axis), the reflection patterns (depicted at the entrance aperture of the system) change into displaced ellipses, the distances of which along the ellipse are no longer circular either. That is to say, three criteria must be satisfied for a centration. Then a centration is obtained along the keratometric axis ("vertex centration"). The vertex is optionally found by the UVL-LVC system and visualized to the user, and they can displace the treatment center onto this vertex by a lateral displacement of the use part of the UVL-LVC system according to the disclosure (that is to say, bring the vertex into the center of the system optical unit or align the keratometric axis coaxially with the system axis).

In the case of option 2, the displacement of the application part by a xy-displacement unit is realized automatically by the system. Thus, this requires algorithms which are able to evaluate the shape of the ellipses and/or the relative position thereof in order to also derive a control signal for the automated displacement direction therefrom. Then, the symmetry condition (largely circular, centered back reflections) can be checked by the system and visually verified by the user. An optional output of the visualization to a user is also possible but not mandatory.

In the case of option 3, the corneal vertex position is determined from the scanning pattern (i.e., the ellipses or rings or circles) and the geometry of the cornea and the geometric data of the system (this may require the shape of the cornea be modeled like a model, e.g., as an ellipsotoric shape). The determined vertex thus is an approximation.

The UVL-LVC system determines the vertex position from the pattern of the back reflection emerging from the known radiated-in ring pattern, that is to say on the basis of the radiated-in circles, from the system geometry, from an eye model and associated eye model parameters (measured or mean values, for example $R_C$, Q-value). Thus, the treatment center can be optionally set fully automatically by the system by way of appropriate scanner offset coordinates (the coordinates for addressing the calculated vertex position) such that the treatment center of the ablation pattern is centered in relation to the vertex position (thus, the user no longer necessarily needs to manually displace the use part in order to bring the vertex into the optical center; instead, the same is displaced to the vertex in order to make the scanning pattern "symmetrical" (see above)). Advantageously, the automatically detected vertex is optionally referenced here to the pupil detected at the same time by way of a co-observation or by way of a dedicated eye tracker. Hence, if a contact interface is used to couple the patient's eye to the UVL-LVC system, even a moderate slippage of the contact interface during the docking process can be compensated, or a reliable automated re-centration in the case of contact interface detachment ("suction loss") is possible after the contact interface has been reapplied.

In some aspects, the principal may be similar to the principle of Placido disk-based topography equipment—albeit with decisive differences: While the image representation of illuminated rings (not directed radiation) is evaluated in the case of Placido disk-based topography equipment so that each point on the cornea is illuminated by different rings and each point on the cornea produces a Purkinje image of each point on the illumination rings, the evaluation in the UVL-LVC system according to the exemplary embodiment explained here is implemented by way of directed irradiation, which in each case produces only a back reflection of beams directed at the cornea. In comparison therewith, only the reflection beam that passes through the nodal point of the camera system (entrance pupil) is detected in the case of conventional Placido disk-based topography equipment. The corneal shape is calculated therefrom and from the associated reflection condition by way of a (typically iterative) construction.

Figure 8:
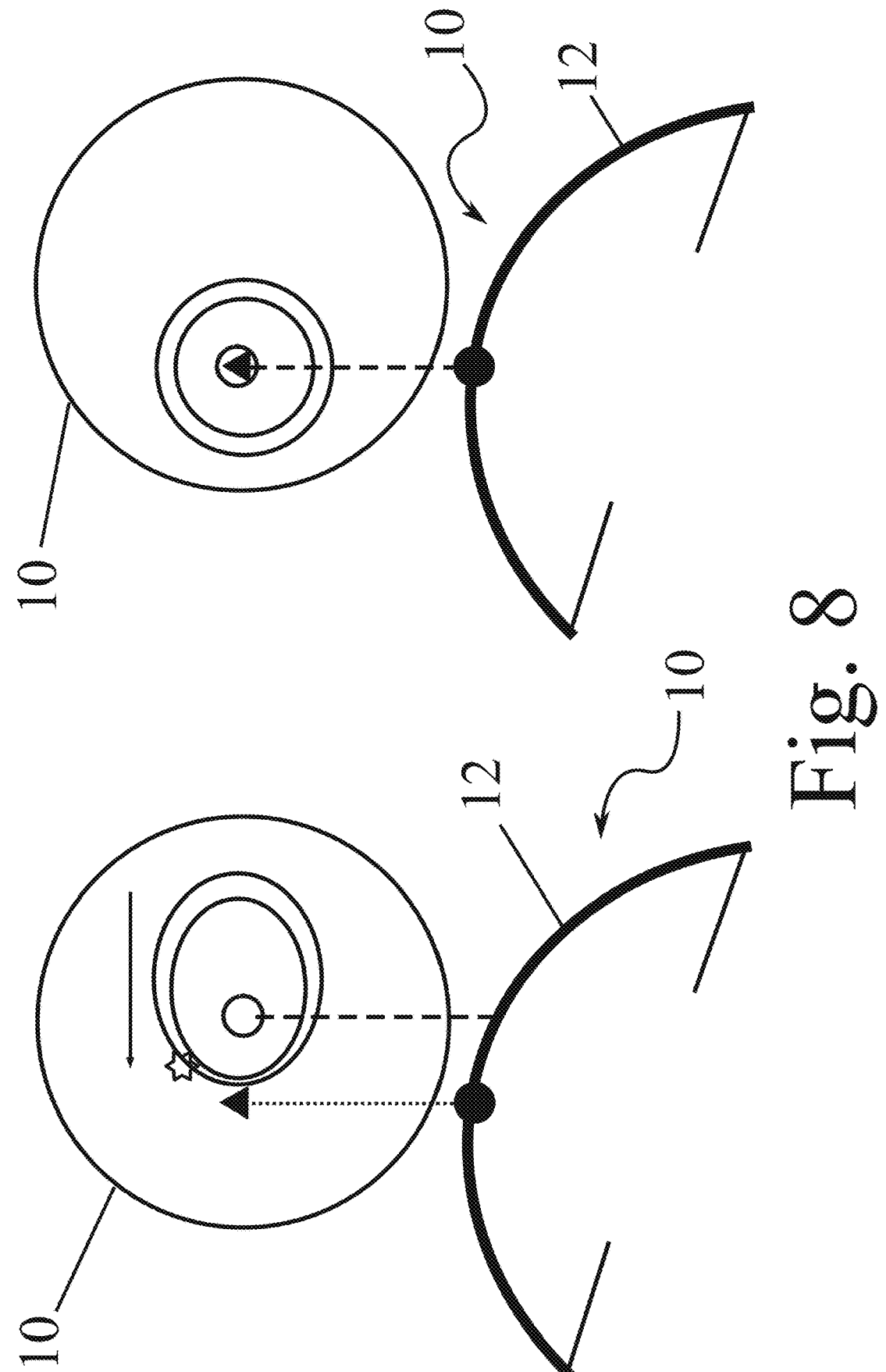
FIG. 8 shows an explanation for the centration on the vertex by radiating-in ring-shaped markings.

According to the aforementioned exemplary embodiment, rings or circles are scanned by the UVL-LVC system. The various situations occurring in the process are depicted in FIG. 8 in exemplary fashion. The precise situation depends here on the irradiation geometry, the eye 10 and the reflection detection geometry, and may therefore deviate from the principle shown. Should the patient's eye under a UVL-LVC system according to the disclosure not be aligned with respect to the keratometric axis, that is to say the connecting line between corneal vertex and fixation target in the case where the patient's eye is coupled to the UVL-LVC system by means of the patient interface, (left partial image) and hence should the keratometric axis not be aligned coaxially with respect to the optical axis of the UVL-LVC system according to the disclosure, the rings passed over by the scanner do not produce circular and symmetric rings as back reflections as a result of the "oblique position" of the eye, that is to say as a result of the incidence of the rays on points with a different angle of incidence. Thus, there is a characteristic deformation of the individual circles and a displacement of scanned circles with a different circle diameter with respect to one another (as indicated; see FIG. 8, with the deformation/displacement of the rings here not reproducing the real conditions).

By contrast, if the system axis of the UVL-LVC system corresponds with the keratometric axis, the situation depicted to the right in FIG. 8 arises. This (like in the topography) is characterized in that the rings become as circular and symmetric (same ring spacings in all directions) as possible and the circles lie centered with respect to the optical system axis. The vertex as a topological landmark on the cornea is then located exactly on the keratometric axis ("vertex centration"). This is due to the fact that, as a rule, the human cornea (without severe pathological changes or trauma) is able to be modeled well by an ellipse (or ellipsotoric shape). By means of suitable corneal models, which may also build on the measured corneal parameters (topography: $R_C$, Q-value, etc.), and with knowledge of the optical geometry it is possible to determine the vertex position on the cornea and hence possible to determine a corresponding scanner offset position, which belongs to the corneal vertex.

The aforementioned features of the disclosure, which are explained in various exemplary embodiments, can be used not only in the combinations specified in an exemplary manner but also in other combinations or on their own, without departing from the scope of the present disclosure.

A description of a piece of equipment relating to method features is analogously applicable to the corresponding method with respect to these features, while method features correspondingly represent functional features of the equipment described.

Figure 9:
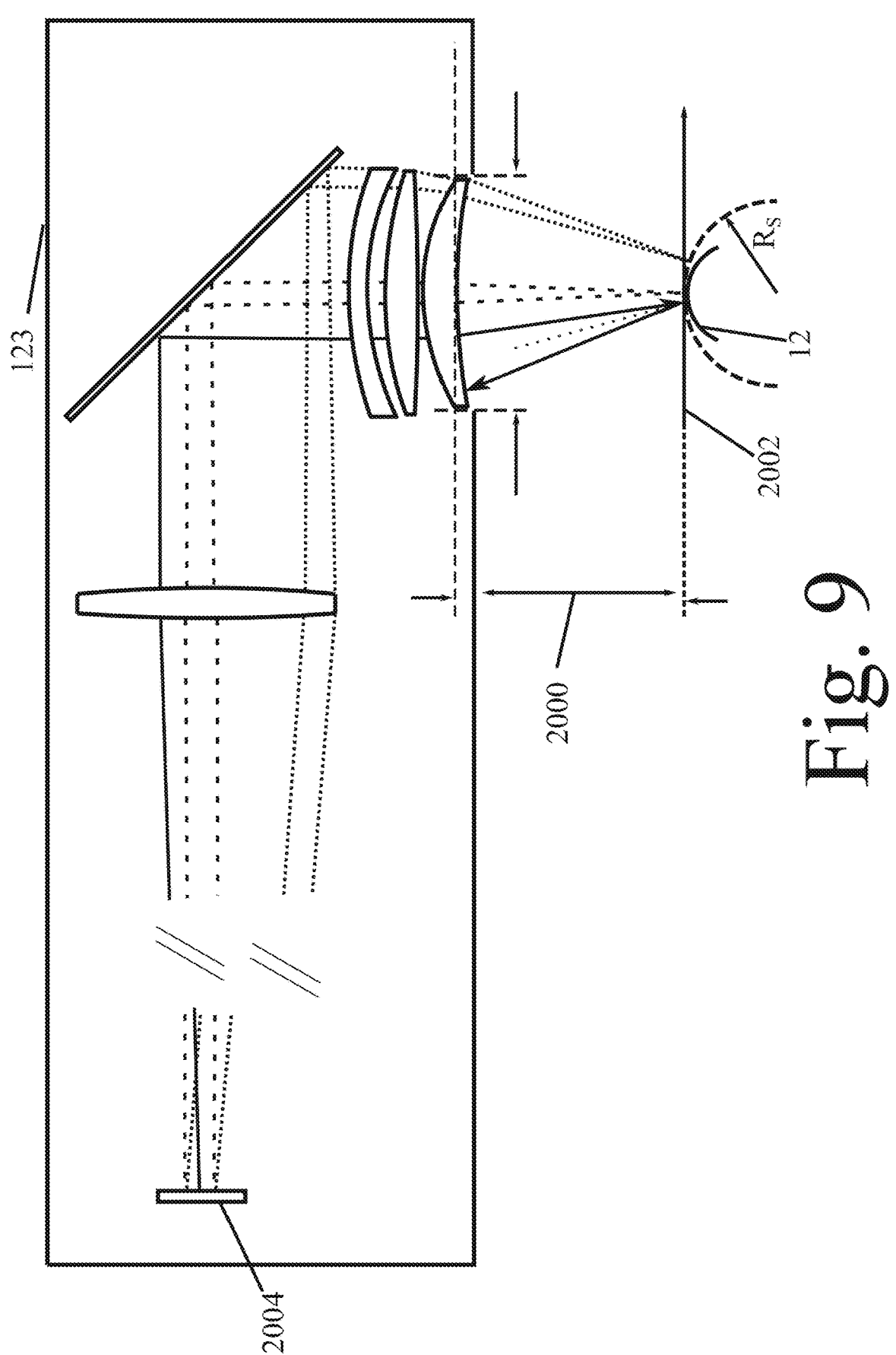
FIG. 9 shows a schematic representation of a beam path of a UVL-LVS system according to an exemplary embodiment.

A further exemplary embodiment of a UVL-LVC system is described in detail below, with reference being made to FIG. 9.

The UVL-LVC system according to the exemplary embodiment comprises an imaging optical unit 124 in the form of a microscope optical unit. The microscope optical unit is composed of two parts (M01 and M02) and was designed such that beam shaping is optimal for suitable focusing (approximately 0.7 mm FWHM) of the UV laser beam for the treatment on the cornea, that is to say in the case of an ablation wavelength of 193 nm. The beam deflector 124c for example allows the visual observation of the eye 10, for example by means of suitable camera imaging. Further, the microscope optical unit was designed for focusing on a focal field radius of curvature $R_S$ of 20 mm (cf. also FIG. 3). In this case, the geometry was chosen (see above) such that the effective optical diameter, that is to say the optical opening, of the microscope optical unit 124 corresponds to approximately 50 mm at the entrance aperture of the use part and a working distance (distance between the image-side vertex of the microscope optical unit and the corneal apex with the work plane WP, cf. also working distance Δ, FIG. 2) of approximately 47 mm arises. In this case, both the therapy beam light and the scanning beam light are deflected by a scanning system in the form of a 2-D scanner (xy-deflection; propagation direction z) (not plotted) and the scanner plane is suitably advanced in the direction of the microscope optical unit 124 (see pupil plane MO, conjugate scanner plane) by way of a relay optical unit ("tube extension," likewise not plotted) such that this plane then represents the pupil plane of the microscope optical unit 124 for focusing along the focal field radius of curvature on the eye. The laser beams 110 are depicted in exemplary fashion for central focusing and peripheral focusing (green and blue dotted rays, respectively). By way of example, an arbitrary scanning beam or centration beam was also plotted. It has already been explained that the UV laser beam for the treatment and the scanning beam or centration beam can be applied simultaneously (in situ scanning during the ablation) or at separate times (e.g., scanning beam with a determination of the reflection patterns; see below, before or after the treatment). The therapy beam light (or the same source) can also be used directly for the scanning beam or centration beam, with it being necessary to consider certain requirements, for example those specified further below (attenuation or beam shaping). If the scanning beam is generated from a separate light source, it is possible to apply similar methods or further known methods for the beam definition. By way of example, the wavelength dispersion in the optical units should then be taken into account for the specific beam paths and the direction of irradiation on the cornea 12 by the scanning beam or centration beam. Additionally, such a case will probably require the adaptation of the beam divergence of the scanning beam or centration beam such that an adequate focus arises in the work plane or the focal field. Otherwise, no sharp focus would arise in the corneal plane in the case of an infrared scanning beam (said focus would be "deeper" in the figure, that is to say below the work plane WP of the therapy beam or UV laser beam if the focal position for 193 nm were in the corneal plane) since the refractive power of the microscope optical unit is less at this wavelength than at 193 nm (positive dispersion assumed).

The back reflection direction (back reflection 126) is determined by the angle of incidence and location of the scanning beam on the cornea and the corneal normal at the location of the irradiation, the latter in turn being determined by the corneal shape. For as long as the back reflection falls into the optical aperture, it is deflected by MO (or only by MO1) and is accessible to a detection at a suitable site (e.g., by output coupling at a further beam splitter downstream of MO1, as seen in the direction of the scanning system, or else directly in front of the scanning system). The precise beam paths of the back reflection through the microscope optical unit and beyond arise in a manner known per se from beam calculations/imaging equations. The locations of incidence of the scanning beams in the work plane (or the focal field locations) are uniquely defined (e.g., as a function of the scanner angle). In the case of a known geometry of the cornea 12 and a known working distance, and also by way of the known imaging by the imaging optical unit 124, a well-defined deflection of the back reflection 126 (or shape and size of the reflection pattern, for example in the case of a circular scan) is therefore also defined at the detector. Attention is drawn to the fact that the reflection patterns shown are the ones resulting from the reflection intersection points in the vertex plane of the optical unit MOL that is to say without the specific back-calculation through the optical unit to the detector, and this is without relevance to the discussion since only the pattern size changes, to a calculable extent, after passing through the optical unit and the detection and there is no change in the symmetry behavior and the conditions in the pattern itself.

The procedure when centering a UVL-LVC system on the vertex of a patient's eye is described below with reference to FIGS. 10A to 10I on the basis of exemplary cases of the analysis of back reflections of radiation radiated-in in the form of annuluses on the cornea by the imaging optical unit, without however restricting the disclosure thereto.

In this case, FIGS. 10A to 10I each show the scanning patterns in the work plane (WP) in front of the eye on the left and the reflection pattern on the right, as the latter would appear in the object-side vertex plane (that is to say still prior to the passage through the optical unit). The coordinate axis on the right-hand side is specified in millimeters. The ring represented by the thick line in the left-hand image represents the optical system axis ("optical axis") and the triangle plotted using the thick line represents the corneal vertex. In the right-hand image, the circle around the coordinate origin represents the entrance aperture of the imaging optical unit on the use part.

Attention is drawn to the following: The same scanner angles were used during the calculation (e.g., circular scan) for the various cases—even at different wavelengths (scanning beam with 193 nm and 840 nm wavelength). As a result of the dispersion in the imaging in the optical unit, this yields different radiated-in positions and angles on the cornea for different wavelengths in the case of the same scanner deflection! All calculations are based on the above-described optical system (containing a relay optical unit). An elliptic corneal model with a Q-value of –0.25 ("prolate property") and a central radius of curvature of 7.86 mm was chosen as the eye model for the reflection calculation.

Figure 10A:
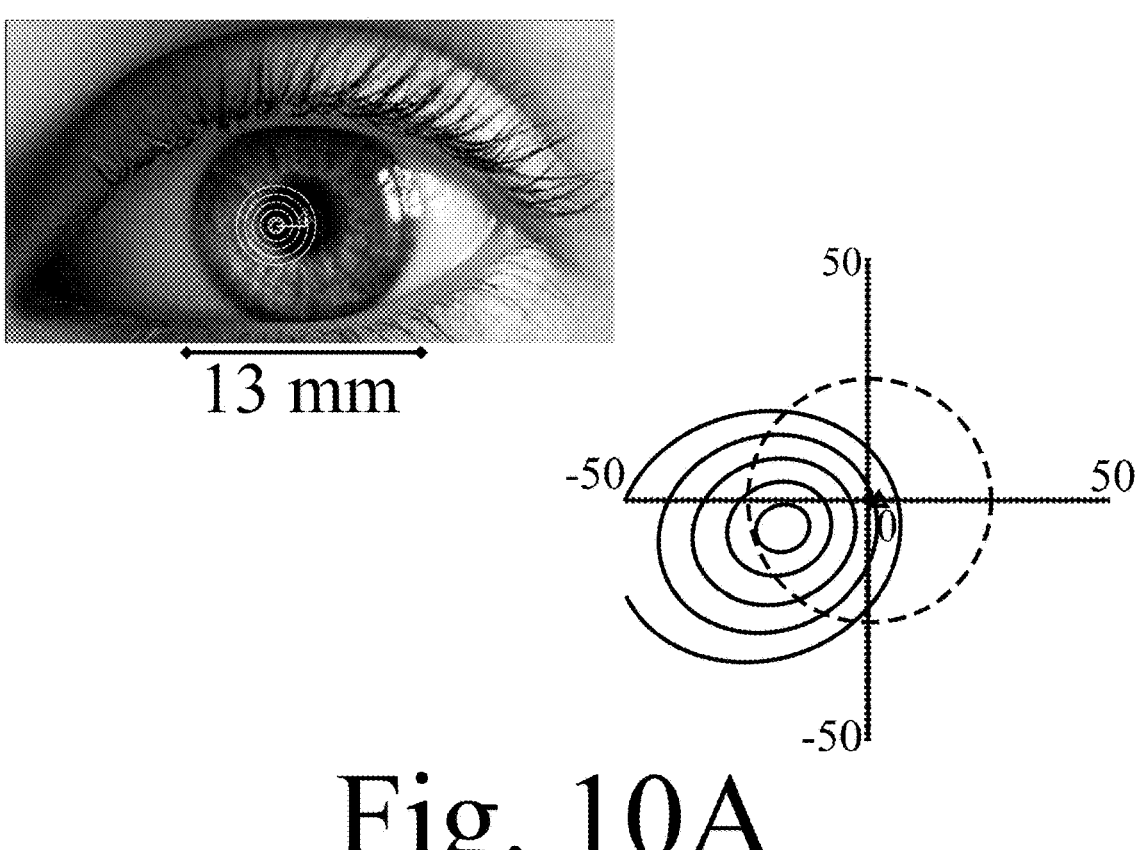
FIG. 10A to 10I show exemplary representations of back reflections of radiated-in rings in the case of a centration on the vertex.

FIG. 10A: Scan of a plurality of circles with different diameters (left-hand image). Displacement of the optical system axis of the use part by 1.5 mm in the horizontal direction ("to the left") and 0.5 mm in the vertical direction ("downward") vis-à-vis the corneal vertex (more precisely the keratometric axis). Ellipses with a characteristic shape, arrangement and position arise in the image of the back reflection in the case of the circular scan. It is evident that the reflections for the chosen scan radii (largest ring in the left-hand image with a 1.78 mm radius) cannot fully return to the system.

The scanning beam wavelength is 193 nm.

Figure 10B:
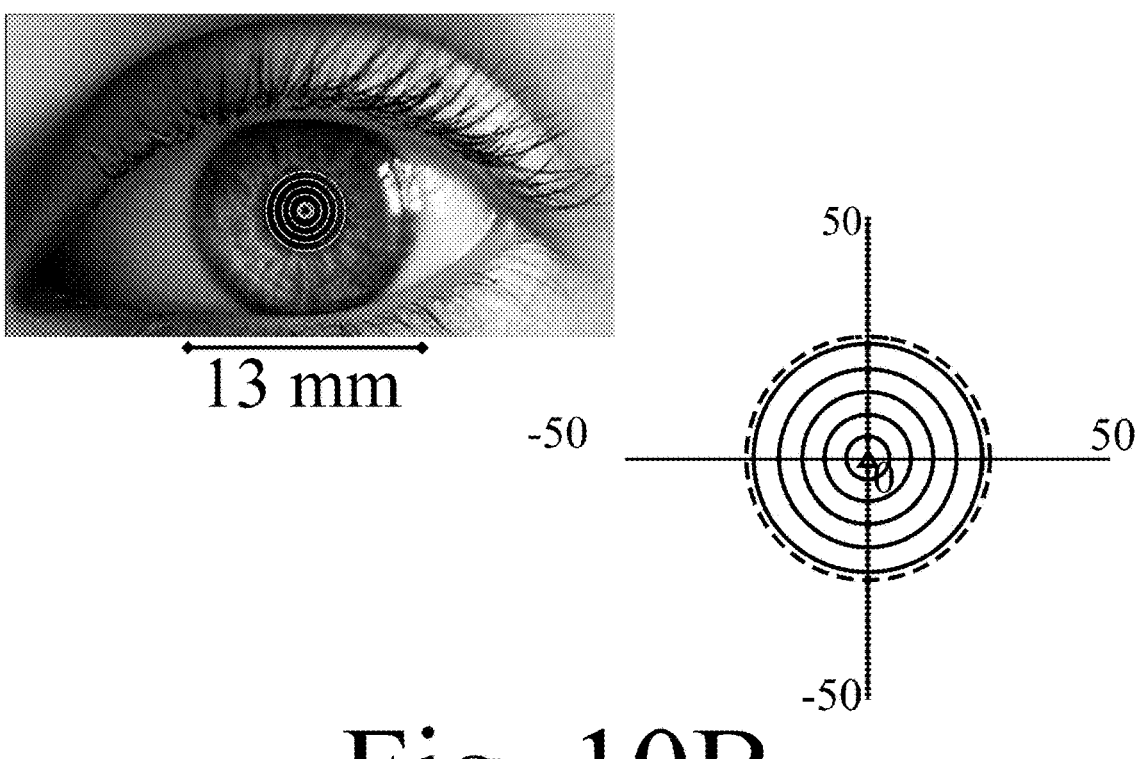

FIG. 10B: Scan of a plurality of circles with different diameters (left-hand image). No displacement of the optical system axis of the use part vis-à-vis the corneal vertex. Circles with the center around the optical system axis likewise arise in the reflection image in the case of the circular scan. It is evident that the reflections for the chosen scan radii (largest ring in the left-hand image with approximately 1.78 mm radius as measured in the work plane) can fully return to the system.

The scanning beam wavelength is 193 nm.

Figure 10C:
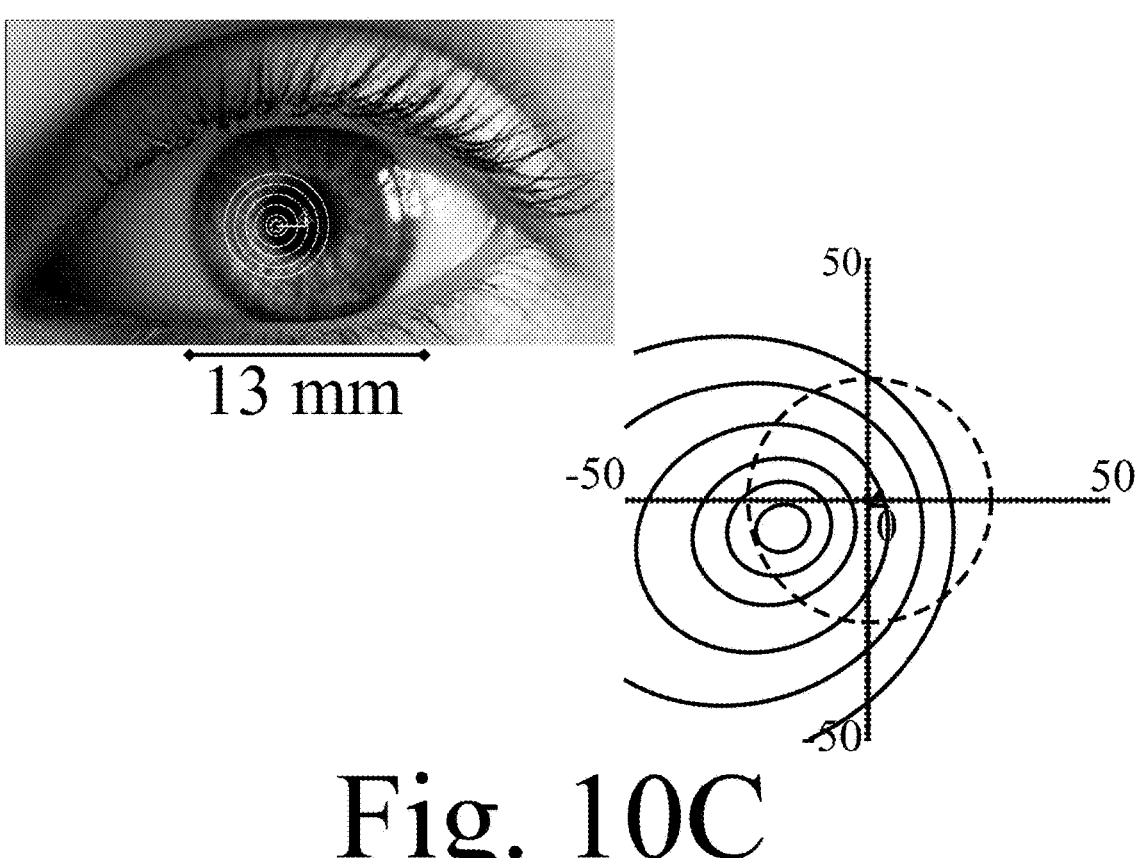

FIG. 10C: Scan of a plurality of circles with different diameters (left-hand image). The larger ring radii (left-hand image) in comparison with case 1 and 2 (193 nm) arise in the case of the same scanner deflection from the modified imaging by the dispersion in the optical unit. Displacement of the optical system axis of the use part by 1.5 mm in the horizontal direction ("to the left") and 0.5 mm in the vertical direction ("downward") vis-à-vis the corneal vertex (more precisely the keratometric axis). Ellipses with a characteristic shape, arrangement and position arise in the reflection image in the case of the circular scan. It is evident that the reflections for the chosen scan radii (largest ring in the left-hand image with a 2.35 mm radius as measured in the work plane) cannot fully return to the system.

The scanning beam wavelength is 840 nm.

Figure 10D:
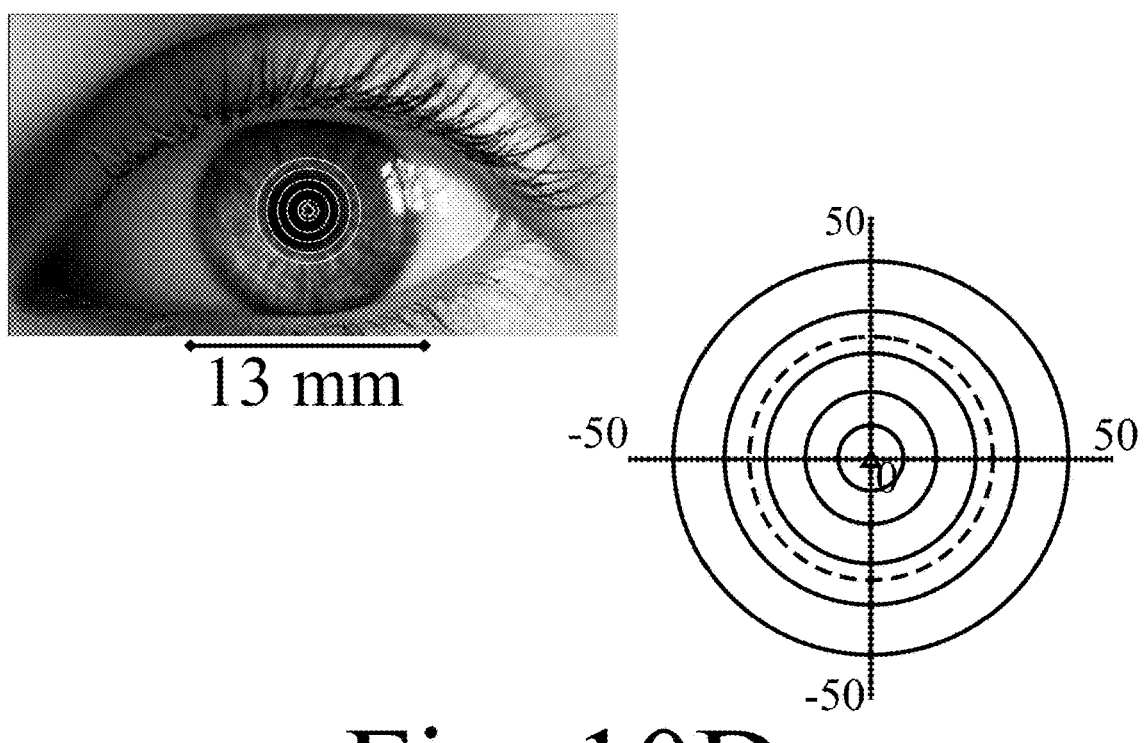

FIG. 10D: Scan of a plurality of circles with different diameters (left-hand image). No displacement of the optical system axis of the use part vis-à-vis the corneal vertex. Circles with the center around the optical system axis likewise arise in the reflection image in the case of the circular scan. It is evident that the reflections for the chosen scan radii (largest ring in the left-hand image with a 2.35 mm radius) cannot fully return to the system.

The scanning beam wavelength is 840 nm.

Figure 10E:
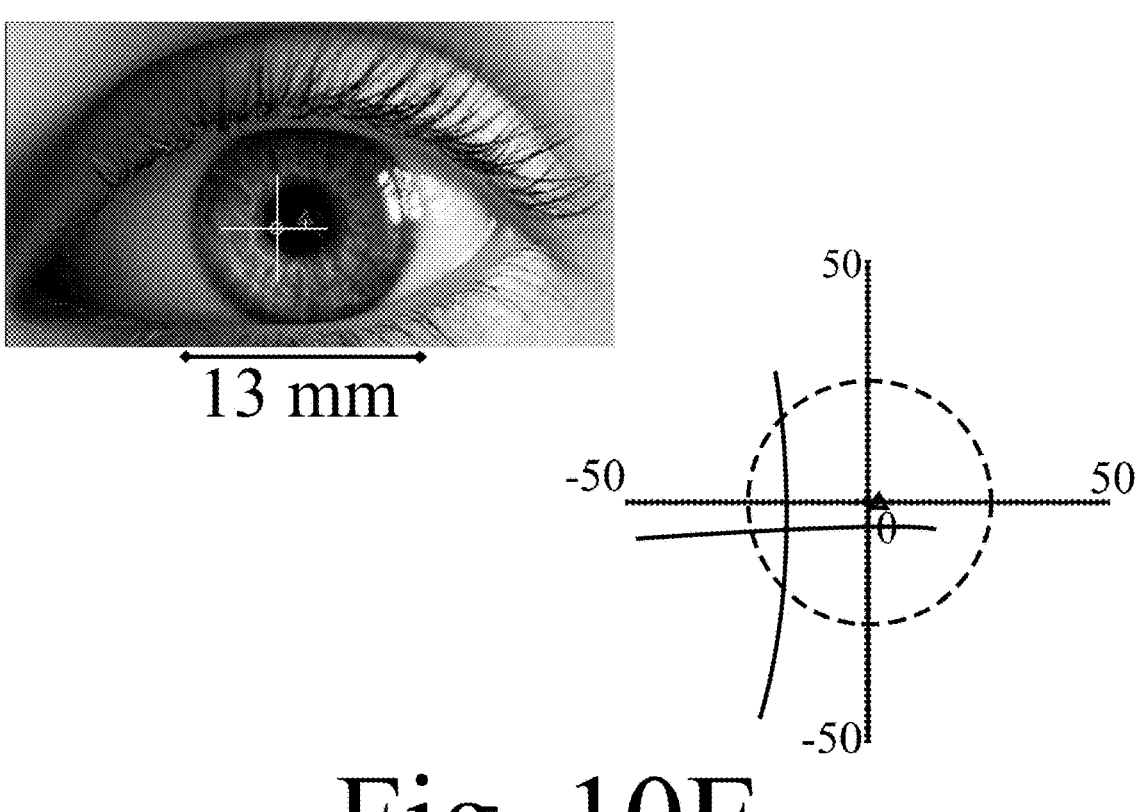

FIG. 10E: Scan of a line in a horizontal and vertical direction, in each case with 5.94 mm length (left-hand image). Displacement of the optical system axis of the use part by 1.5 mm in the horizontal direction ("to the left") and 0.5 mm in the vertical direction ("downward") vis-à-vis the corneal vertex. "Concealed lines displaced in relation to the system axis" arise in the reflection image. It is evident that the reflections for the deflection (line length) cannot fully return to the system.

The scanning beam wavelength is 193 nm.

Figure 10F:
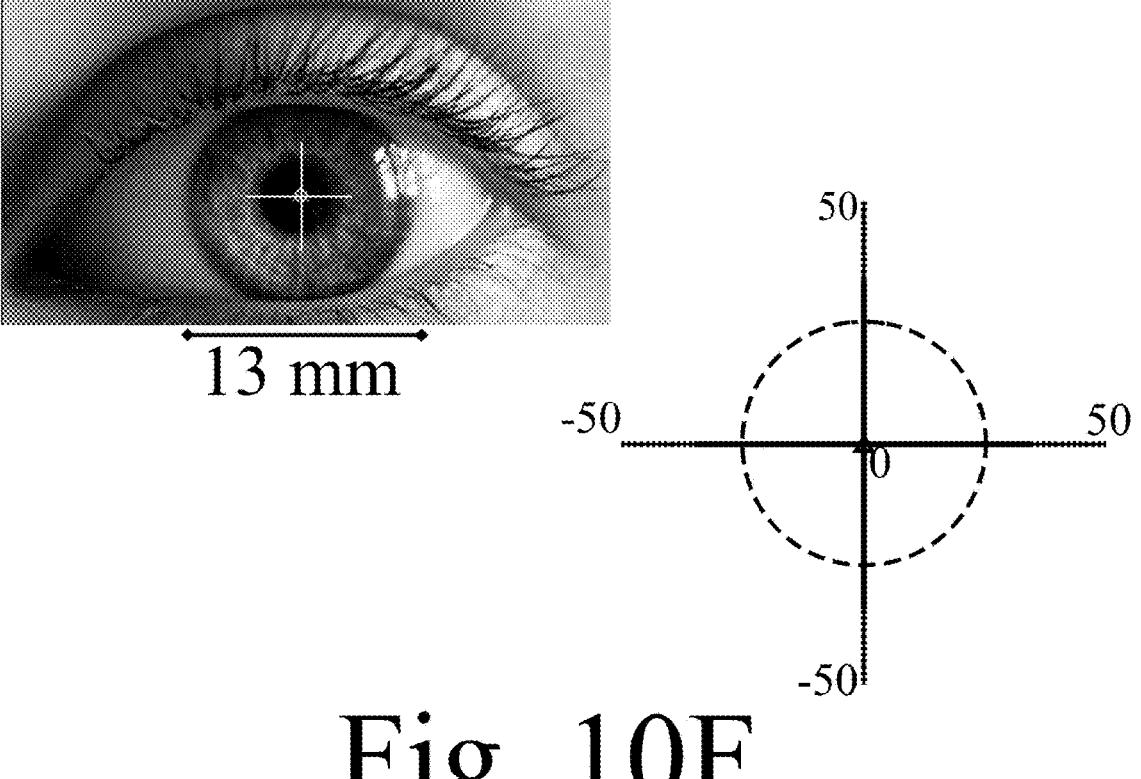

FIG. 10F: Scan of a line in a horizontal and vertical direction, in each case with 5.94 mm length (left-hand image). No displacement of the optical system axis of the use part vis-à-vis the corneal vertex. Straight lines with the center on the optical system axis arise again in the reflection image. It is evident that the reflections for the deflection (line length) cannot fully return to the system. This would be the case up to a line length of 3.56 mm (cf. circular scan).

The scanning beam wavelength is 193 nm.

Figure 10G:
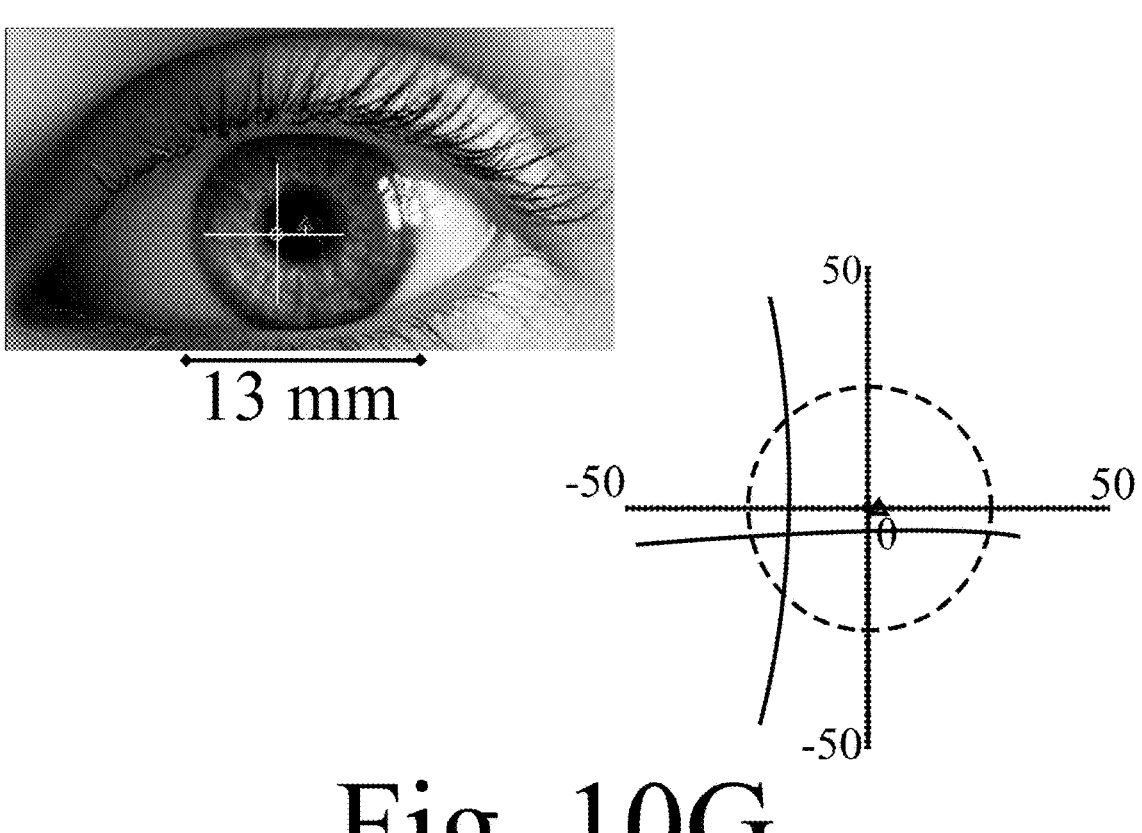

FIG. 10G: Scan of a line in a horizontal and vertical direction, in each case with 7.82 mm length (left-hand image). The longer line length (left-hand image) in comparison with case 5 and 6 (193 nm) arises in the case of the same scanner deflection from the modified imaging by the dispersion in the optical unit. Displacement of the optical system axis of the use part by 1.5 mm in the horizontal direction ("to the left") and 0.5 mm in the vertical direction ("downward") vis-à-vis the corneal vertex (more precisely the keratometric axis). "Concealed lines" displaced in relation to the system axis arise in the reflection image. It is evident that the reflections for the deflection (line length) cannot fully return to the system.

The scanning beam wavelength is 840 nm.

Figure 10H:
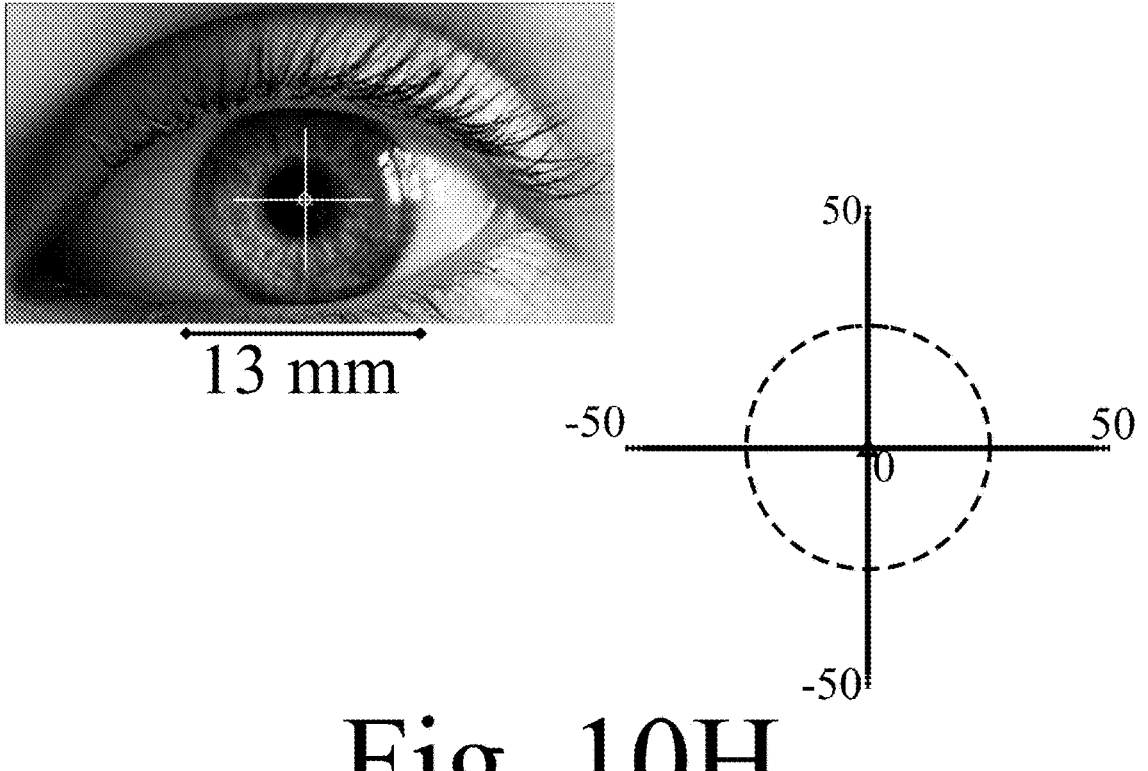

FIG. 10H: Scan of a line in a horizontal and vertical direction, in each case with 7.82 mm length (left-hand image). No displacement of the axis of the optical system axis of the use part vis-à-vis the corneal vertex. Straight lines with the center on the optical system axis arise again in the reflection image. It is evident that the reflections for the deflection (line length) cannot fully return to the system.

The scanning beam wavelength is 840 nm. The region on the cornea able to be scanned is once against smaller in comparison with 193 nm (cf. circular scan).

If the eye is displaced in the work plane (in cases 1 to 8) vis-à-vis the use part or the imaging optical unit (see, e.g., FIG. 10A), there is a change in the reflection pattern or the back reflection in a calculable and defined manner. Scanned circles (FIG. 10A, left) become ellipses (in the vertex plane of the optical unit) (FIG. 10A, right). The lateral displacement of the use part vis-à-vis the eye now allows the reflection pattern to be "made more symmetrical." In the example above, ellipses (FIG. 10A, right) without equidistant distances and without centration in relation to the optical axis would then become circles (FIG. 10B, right) with radially equidistant distances (like in the case of Placido topography) if the optical system axis becomes coaxial with the keratometry axis (vertex centration). Then, the circle centers are thus also located on the optical system axis. Observation: More precisely, approximately circles would be obtained for real eyes. This is a due to the remaining irregularities of the eye or the deviation of the real corneal shape from the model shape, which plays no role in practice for as long as this does not relate to the determination of the topography of the cornea itself. However, the deviation from the circular shape would be below a predetermined threshold value in this case.

It is also evident that the choice of the scanning wavelength has no influence on the general symmetry conditions, for example from comparing the cases in FIGS. 10A, 10B with 10C and 10D for 193 nm and 840 nm scanning beam wavelength and centration beam wavelength, respectively. However, without further measures a scanning beam wavelength close to or equal to the therapy beam wavelength is more advantageous since this allows the reflections to be captured from a larger region on the cornea. It is insinuated here that the optical unit and focus position were optimized for 193 nm.

Evidently, equivalent relationships arise for the line scan (see the cases in FIGS. 10E, 10F, 10G, and 10H). It is also evident from this case that the direction of the scanned lines are aligned to the best possible extent along the principal axes of the cornea since additional small deformations of the lines may otherwise occur (corneal astigmatism). As a rule, the input of the cornea k-values is envisaged in the case of refractive laser systems since these are also required for other purposes, for example the optimization of the ablation profiles. Conversely, the additional deformations of the lines (or a rotation of the line axis with analysis of the line shape) can also be used to determine or verify the k-values by means of a simple ellipsotoric corneal model. This can also be used to determine or monitor the cyclorotation of the eye. This is of interest because conventionally special reference data have to be determined with the diagnosis for this purpose, which reference data then have to be compared to current data, for example of the eye tracker. This can be dispensed with according to an exemplary embodiment of the disclosure since, in principle, it is only the keratometry values (see above, k-values, principal curvature radii) of the cornea that need to be known; as a rule, these are known and considered in every refractive-surgical intervention on the cornea as standard information.

Figure 10I:
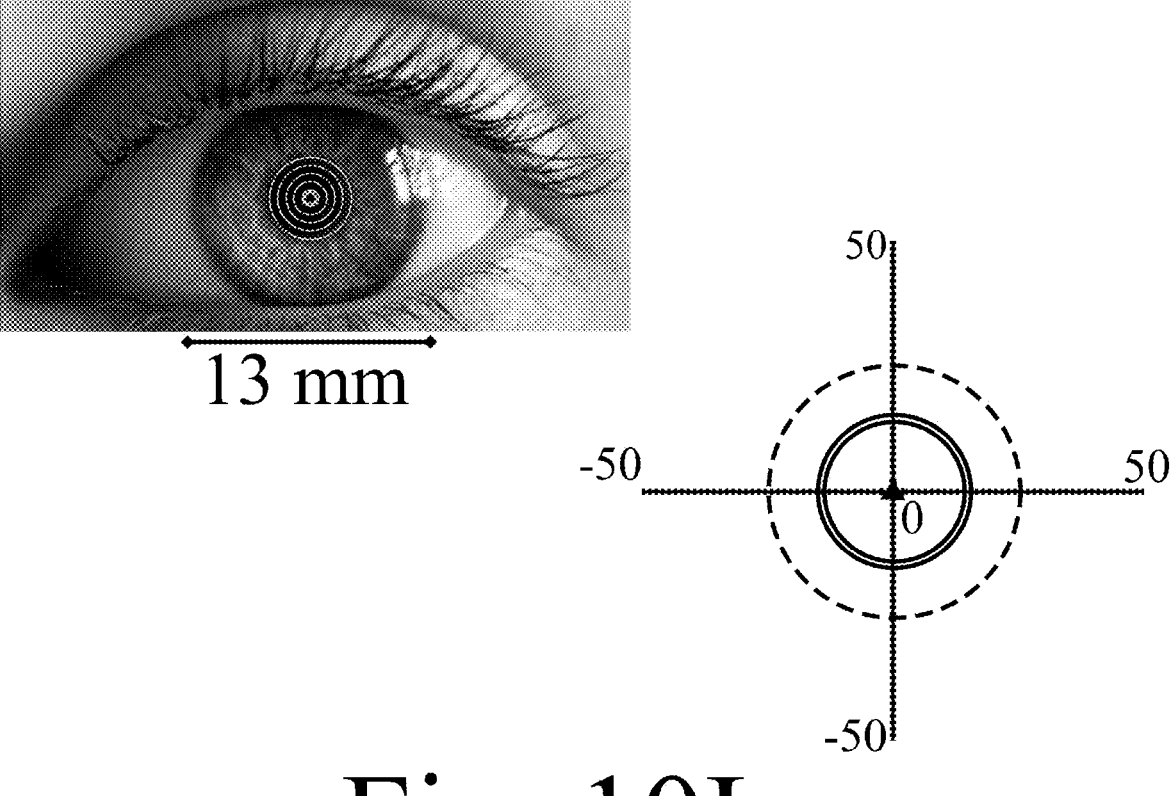

FIG. 10I: Scan of a circle for two different distances from the eye. The centered case (see the case in FIG. 10B above) was considered only to provide better overview. The small circle in the right-hand graph corresponds to the third ring (counted from the center) of the case in FIG. 10B, with an exact working distance. The circle just outside this arises, in the case of the same scanning angle, when the eye is displaced 2 mm in the direction of the optical aperture of the system.

For the centration, the eye itself need not necessarily be at the optimal (i.e., the accurate) working distance. Nevertheless, the symmetry or shape of the reflection pattern is maintained but the size of same changes (or the deflection of the detected reflection on the detector changes), as shown for the case in FIG. 10I. Only the centered case was shown for reasons of simplicity. However, equivalent conditions arise for the non-centered case. The centration of the eye itself in the work plane is attainable and defined purely by the symmetry conditions (e.g., equidistant circles centered on the optical system axis).

In the case of a known corneal geometry (k-values, radii of curvature, for example from the topography), it is precisely also possible to determine the distance of the eye from, or the vertical displacement of the cornea (or of the vertex) vis-à-vis, the work plane, that is to say the deviation of the eye from the working distance of the system, from the deviation from the expected shape or, in particular, the size (stretch) of the reflection pattern. In this case, elliptic or ellipsotoric functions are suitable corneal models. The latter are closer to the real corneal shape with different corneal curvatures on two perpendicular meridians (corneal astigmatism). Other models, as are also used in diagnostic equipment, are likewise conceivable. It would also be possible to use the topography actually determined by presurgery diagnostics. Then, the reflections would be calculated on the basis of precisely this topography (the basic shape of which for non-pathological corneas is, as a rule, very well describable by an ellipsotoric model). Therefore, the method can also be used in principle to set the correct working distance. To this end, the reflection pattern determined on the basis of the corneal geometry (e.g., in the case of an otherwise centered adjustment of the use part relative to the eye, vertex centration) is determined vis-à-vis the target pattern. This method can also be carried out in the case of a non-centered alignment. To this end, algorithms are advantageous which, in particular, consider the "enlargement" within the scope of, e.g., affine transformations regarding the parallel/shear dilation and, from this, determine the deviation of the eye from the working distance. An insufficient adjustment of the distance can be determined or monitored, and may also be indicated. For the centered case, this is also very evident from trigonometric considerations since the system knows the reflection angle (determined) and the opposite leg (likewise determined) as well as the point of incidence distance from the optical system axis in the work plane (geometry of the scanning beam deflection), calculated back to the conditions as far as the object-site vertex plane of the lens. Hence, the adjacent leg which defines the distance is also determined.

Optionally, the working distance is actively set by the user in the case of UVL-LVC system, with, e.g., crossed distance lasers being used and/or a sharp image representation of the eye on the camera being assessed. Various methods are used in this case. However, once the working distance has been set exactly, it is possible to conversely determine the geometry of the corneal surface from the reflection pattern, for example on the basis of an ellipsotoric model. By way of example, a least squares minimization could be used to this end, within the scope of which the corneal model parameters are varied until the deviation between measured reflection pattern and model-based calculated reflection pattern (in the case of a known corneal distance=working distance) becomes minimal under the known optical beam imaging/geometry. Other or similar known methods are evidently revealed to a person skilled in the art since the procedure would be similar to, e.g., the case of a keratometer or other diagnostic systems and equipment for corneal measurement (e.g., IOL-Master by Zeiss).

From a combination of measuring the reflection pattern of a circular scan and measuring the reflection belonging to the central scanning beam (scanning beam incident on the optical system axis), it is possible in the case of a centration either in relation to the vertex or in relation to the CSCLR condition to possibly determine the difference between vertex and ophthalmic pole (or the deviation between the visual axis and the keratometric axis).

Moreover, the disclosure comprises the subject matter of the following clauses:

Clause 1. A UV laser-based system for refractive error correction (UVL-LVC system), comprising a UV laser source which emits preferably pulsed laser radiation, a scanning system for lateral scanning of the laser radiation in the x- and y-directions, and preferably also in the z-direction, a control unit, an imaging optical unit comprising a microscope optical unit for focusing the preferably pulsed laser radiation on the cornea of a patient's eye, the optical opening of said optical unit is designed such that an acceptance angle for back reflections $\chi_{Max}$ detectable by the UVL-LVC system according to the disclosure of greater than 15°, preferably greater than 25° and particularly preferably greater than or equal to 37° is achievable.

Clause 2. The UVL-LVC system according to clause 1, the optical opening of which is greater than 50 mm, preferably greater than or equal to 60 mm, and the working distance of which is less than 50 mm, preferably less than or equal to 40 mm.

Clause 3. The UVL-LVC system according to clause 1 or 2, the imaging optical unit of which contains an objective for imaging the laser radiation in a focal field, with the objective comprising a lens formed to provide a convergent focal field.

Clause 4. The UVL-LVC system according to any one of clauses 1 to 3, furthermore comprising a contact interface for coupling the patient's eye to the UVL-LVC system.

Clause 5. The UVL-LVC system according to any one of clauses 1-3, designed to determine the axial distance between the cornea and the optical system.

Clause 6. The UVL-LVC system according to any one of clauses 1 to 4, furthermore comprising a detection system for the incoming and returning beams, preferably a narrow-band scanning beam, scan and position evaluation algorithms, and algorithms for the reflection analysis.

Clause 6a. The UVL-LVC system according to any one of clauses 1 to 4, wherein the scanning beam operates in the IR range or in the visible spectrum.

Clause 7. The UVL-LVC system according to any one of clauses 1 to 4, wherein the scanning beam operates in the UV range and preferably corresponds to the significantly attenuated ablation laser beam (object HV), and is preferably adjusted by pinholes and suitable refractive optical elements to the detection plane (object CZM).

Clause 7a. The UVL-LVC system according to clauses 5 to 7, configured to detect the position of the Purkinje image as an offset position.

Clause 8. The UVL-LVC system according to clause 7, configured to use the position of the Purkinje image for automated centration or for the manual alignment of the system according to the CSCLR condition.

Clause 9. The UVL-LVC system according to clause 8, which in the case of an automated centration has an algorithm for calculating a centration-corrected fluence loss function.

Clause 10. A method for centering a UVL-LVC system, wherein the knowledge of the geometry of the optical imaging and knowledge of the focal field radius of curvature $R_S$ and of the corneal radius of curvature $R_C$ are used to determine the position of a "symmetric beam pair" of incident beam and detected back reflection (Purkinje image) and the associated scanner position, as a result of which the offset position of the corneal point belonging to the CSCLR condition in relation to the optical axis of the system is given, and hence an automated centration is realized by the scanner with an allowance in relation to the offset position, with the axial distance between cornea and optical system preferably also being considered here.

Clause 11. The method for centering a UVL-LVC system according to clause 10, wherein the offset position is used to convert the scan coordinates for the ablation pulses such that these are correct for the ablation of the eye, even if the system is not positioned coaxially with respect to the CSCLR condition.

Clause 12. The method for centering a UVL-LVC system according to clause 10 or 11, wherein the offset position is continuously updated during a treatment by means of a correction signal from an eye tracker.

Clause 13. A UV laser-based system for refractive error correction (UVL-LVC system), comprising a UV laser source which emits preferably pulsed laser radiation, a scanning system for lateral scanning of the laser radiation in the x- and y-directions, and preferably also in the z-direction, a control unit, an imaging optical unit comprising a microscope optical unit for focusing the preferably pulsed laser radiation on the cornea of a patient's eye, the optical opening of said optical unit is designed such that an acceptance angle for back reflections $\chi_{Max}$ detectable by the UVL-LVC system according to the disclosure of greater than 15°, preferably greater than 25° and particularly preferably greater than or equal to 37° is achievable.

Clause 14. The UVL-LVC system according to clause 13, the optical opening of which is greater than 50 mm, preferably greater than or equal to 60 mm, and the working distance of which is less than 50 mm, preferably less than or equal to 40 mm.

Clause 15. The UVL-LVC system according to clause 13 or 14, the imaging optical unit of which contains an objective for imaging the laser radiation in a focal field, with the objective comprising a lens formed to provide a convergent focal field.

Clause 16. The UVL-LVC system according to any one of clauses 13 to 15, furthermore comprising a contact interface for coupling the patient's eye to the UVL-LVC system.

Clause 17. The UVL-LVC system according to any one of clauses 13 to 16, furthermore comprising a detection system for the incoming and returning beams, preferably a scanning beam, scan and position evaluation algorithms, and algorithms for the reflection analysis.

Clause 18. The UVL-LVC system according to clause 17, configured to determine an offset position in relation to the vertex by scanning circles on the cornea of the patient's eye and by analyzing the reflections, i.e., deformed rings detected by the UVL-LVC system according to the disclosure.

Clause 19. The UVL-LVC system according to clause 18, configured to scan circles with a different diameter in the process and to determine the displacement and deviation thereof (deformation) from a circular shape, with the system axis of the UVL-LVC system according to the disclosure corresponding to the keratometric axis and hence to the position of the vertex when no displacement or deformation can be determined.

Clause 20. The UVL-LVC system according to clause 18 or 19, configured to use the position of the vertex (or the offset position therefrom) for automated centration of the treatment coordinates or for the manual alignment of the UVL-LVC system.

Clause 21. The UVL-LVC system according to clause 20, which in the case of an automated centration has an algorithm for calculating a centration-corrected fluence loss function.

Clause 22. The UVL-LVC system according to clause 20 or 21, comprising an eye tracking system and being able to evaluate the coordinates of the tracked eye positions in relation to the determined vertex position.

Clause 23. A method for centering a UVL-LVC system, in which the position of the vertex (or the offset position therefrom) is determined by scanning circles on the cornea of the patient's eye and by the analysis of the reflections, i.e., deformed rings detected by the UVL-LVC system according to the disclosure, the offset position is used to realize an automated centration by the scanner with an allowance in relation to the offset position or a manual centration.

Clause 24. The method for centering a UVL-LVC system according to clause 23, wherein the offset position is used to convert the scan coordinates for the ablation pulses such that these are correct for the ablation of the eye, even if the system is not positioned coaxially with respect to the CSCLR condition.

Clause 25. The method according to clause 23 or 24, wherein the determined offset position can preferably be compared simultaneously to the tracking coordinates of an eye tracked by means of an eye tracker such that even in the case of a non-fixated eye the determined vertex position and the treatment positions centered thereon remain rigid within a coordinate system that moves with the eye.

LIST OF REFERENCE SIGNS

10 Patient's eye
12 Cornea
14 Fovea
16 Visual axis/optical axis of the eye
18 Ablation profile
20 Scanning system
22 Fixation element
24 Ophthalmic pole
100 UVL-LVC system
102 UV laser source
104 Scanner or scanning system
106 Control unit
108 Planning unit
110 Laser beam
112 Excimer laser
114 Attenuator
116 Deflector
118 Stop
120 Beam shaper
122 Rotary joint
123 Use part
124 Imaging optical unit
124$a$ First lens group of the imaging optical unit
124$b$ Second lens group of the imaging optical unit
124$c$ Deflector
126 Back reflection
1000 Optical opening of the imaging optical unit
1002 Working distance of the imaging optical unit
2000 Working distance
2002 Work plane
2004 Scanning system
$\chi$ Opening angle of the back reflection
$\chi_{max}$ Maximally detectable opening angle of the back reflection or acceptance angle of the imaging optical unit
$R_S$ Focal field radius of curvature
$R_C$ Corneal radius of curvature
$R_A$ Difference radius of curvature
CV Vertex

The invention claimed is:

1. A UV laser-based system for vision correction (UVL-LVC system) of a patient's eye, the UVL-LVC system comprising:
   a UV laser source emitting laser radiation for treating the patient's eye;
   an imaging optical unit focusing the laser radiation on the cornea of the patient's eye, the imaging optical unit being configured to allow a detection of a back reflection of radiation radiated on the cornea of the patient's eye by the imaging optical unit and at least partially reflected by the cornea of the patient's eye, within an acceptance angle $\chi_{Max}$ of at least 2.5°.

2. The UVL-LVC system as claimed in claim 1, wherein the imaging optical unit is configured such that the acceptance angle $\chi_{Max}$ is greater than 5°.

3. The UVL-LVC system as claimed in claim 1, wherein the imaging optical unit includes a microscope optical unit.

4. The UVL-LVC system as claimed in claim 1, wherein the imaging optical unit has an optical opening and has a given working distance, a diameter of the optical opening being greater than or equal to the given working distance.

5. The UVL-LVC system as claimed in claim 1, wherein the imaging optical unit has an optical opening with a diameter of at least 50 mm, and wherein the imaging optical unit has a working distance less than 50 mm.

6. The UVL-LVC system as claimed in claim 1, further comprising a contact interface for coupling the patient's eye to the UVL-LVC system.

7. The UVL-LVC system as claimed in claim 1, wherein the UV laser source is configured to emit pulsed laser radiation and/or wherein the UV laser source includes an excimer laser.

8. The UVL-LVC system as claimed in claim 1, further comprising a scanning system for laterally scanning the laser radiation in the x- and y-directions.

9. The UVL-LVC system as claimed in claim 8, wherein the UVL-LVC system is configured to output couple the back reflection of the radiation detected by the imaging optical unit from the beam path of the laser radiation between the imaging optical unit and the scanning system.

10. The UVL-LVC system as claimed in claim 8, wherein the UVL-LVC system is configured to output couple the back reflection of the radiation detected by the imaging optical unit from the beam path of the laser radiation with the imaging optical unit.

11. The UVL-LVC system as claimed in claim 1, further comprising a detection system for returning beams formed by a detected back reflection of radiation radiated on the cornea of the patient's eye by the imaging optical unit and at least partially reflected by the cornea of the patient's eye.

12. The UVL-LVC system as claimed in claim 11, wherein the centration beam has, or consists of, a spectrum in the infrared and/or visible spectral range.

13. The UVL-LVC system as claimed in claim 12, wherein the centration beam has, or consists of, a spectrum in the ultraviolet spectral range.

14. The UVL-LVC system as claimed in claim 1, further comprising a control unit.

15. The UVL-LVC system as claimed in claim 1, wherein the imaging optical unit is configured to provide a convergent focal field.

16. The UVL-LVC system as claimed in claim 15, wherein the imaging optical unit contains an objective for imaging the laser radiation in a focal field and wherein the objective contains a lens formed to provide the convergent focal field.

17. The UVL-LVC system as claimed in claim 15, wherein the convergent focal field has a focal field diameter of at least 6 mm.

18. The UVL-LVC system as claimed in claim 15, wherein each location in the convergent focal field has a local center of curvature on the side facing away from the imaging optical unit and wherein each location in the focal field preferably has a focal field curvature with a radius $R_S$ ranging from 8 mm to 50 mm.

19. The UVL-LVC system as claimed in claim 15, wherein the imaging optical unit is configured to enable perpendicular impingement of a curved surface with the laser radiation, the curved surface having a local center of curvature on the side facing away from the imaging optical unit at each location, and wherein the curved surface has a diameter of at least 6 mm and/or a surface curvature with a radius $R_F$ ranging from 8 mm to 50 mm.

20. The UVL-LVC system as claimed in claim 1, further comprising a distance determination unit which is designed to determine a distance between the imaging optical unit and the curved surface or the cornea of the patient's eye.

21. The UVL-LVC system as claimed in claim 1, wherein the UVL-LVC system is configured to detect a Purkinje image in an angular range of at least 2.5° by detecting the back reflection of the radiation radiated on the cornea of the patient's eye by the imaging optical unit and at least partially reflected by the cornea of the patient's eye.

22. The UVL-LVC system as claimed in claim 21, wherein the UVL-LVC system is configured to detect a first Purkinje image in an angular range of at least 2.5°.

23. The UVL-LVC system as claimed in claim 21, wherein the UVL-LVC system is configured to use the detected Purkinje image for automated centration and/or manual alignment of the UVL-LVC system.

24. The UVL-LVC system as claimed in claim 23, wherein the UVL-LVC system is configured to carry out the automated centration with an algorithm for calculating a centration-corrected fluence loss function.

25. The UVL-LVC system as claimed in claim 21, wherein the UVL-LVC system is configured to determine a detected position of the Purkinje image as an offset position, with the offset position characterizing a centration that deviates from the CSCLR condition.

26. The UVL-LVC system as claimed in claim 1, further comprising a radiation source for providing a centration beam in the form of one or more circles to be radiated on the cornea of the patient's eye by the imaging optical unit and a control unit designed to detect and analyze the back reflection of the radiation radiated in in the form of the circle or circles.

27. The UVL-LVC system as claimed in claim 26, further comprising a scanning system, with the centration beam in the form of one or more circles being provided with a punctiform centration beam and a deflection movement by way of the scanning system.

28. The UVL-LVC system as claimed in claim 26, wherein the analysis of the back reflection of the circle or circles comprises an analysis of a deviation of the shape of the back reflection from the shape of the circle or circles of the radiated-in radiation.

29. The UVL-LVC system as claimed in claim 28, wherein the control device is configured to determine a correspondence of a system axis of the UVL-LVC system with the keratometric axis of the patient's eye when the deviation of the shape of the back reflection from the shape of the circle or circles of the radiated-in radiation is below a given threshold value or equal to zero.

30. The UVL-LVC system as claimed in claim 29, wherein the system axis of the UVL-LVC system runs through a vertex of the patient's eye when the deviation of the shape of the circle or circles of the back reflection from the shape of the circle or circles of the radiated-in radiation is below a given threshold value or equal to zero.

31. The UVL-LVC system as claimed in claim 26, wherein respective circles of the plurality of circles have different diameters.

32. The UVL-LVC system as claimed in claim 1, wherein the control unit is configured to carry out an algorithm for calculating a centration-corrected fluence loss function.

33. A method for centering a UV laser-based system for vision correction (UVL-LVC system) for a patient's eye, the method comprising:

radiating a centration beam on the cornea of the patient's eye by an imaging optical unit;

detecting a back reflection of a part of the radiated-in centration beam reflected by the cornea by means of the imaging optical unit, the back reflection being detected in an angular range of at least 2.5°; and determining a positioning and/or orientation of the UVL-LVC system relative to the patient's eye on the basis of the detected back reflection.

34. The method as claimed in claim 33, wherein the imaging optical unit is arranged at an axial working distance from the cornea of 50 mm or less when the centration beam is radiated in and when the back reflection is detected.

35. The method as claimed in claim 33, wherein the imaging optical unit has an optical opening that is greater than or equal to the working distance of the imaging optical unit.

36. The method as claimed in claim 33, wherein radiating the centration beam on the cornea of the patient's eye by an imaging optical unit is implemented in such a way that the centration beam has a convergent focal field with a radius of curvature $R_S$.

37. The method as claimed in claim 36, wherein the determination of the positioning and/or orientation of the UVL-LVC system relative to the patient's eye comprises an analysis of the detected back reflection, and wherein the determination of the positioning and/or orientation of the UVL-LVC system relative to the patient's eye is implemented using the radius of curvature $R_S$ of the convergent focal field, a predetermined corneal radius of curvature $R_C$ of the patient's eye and an axial distance between the cornea and the imaging optical unit.

38. The method as claimed in claim 36, wherein radiating in the centration beam comprises a lateral scanning of the centration beam in the x- and y-directions with a scanning system and a determination of associated settings of the scanning system.

39. The method as claimed in claim 36, wherein the centration beam has a parallel beam and the detection of the back reflection comprises a detection of a first Purkinje image of the parallel beam.

40. The method as claimed in claim 39, further comprising:

determining an offset position on the basis of the detected Purkinje image, the offset position characterizing a centration that deviates from a CSCLR condition.

41. The method as claimed in claim 40, further comprising:

determining an allowance of the UVL-LVC system in relation to the offset position.

42. The method as claimed in claim 41, further comprising:

determining adjusted coordinates for laser radiation to be radiated in for the treatment of the patient's eye whilst taking the offset position and the deviation from a centration according to the CSCLR condition connected therewith into account.

43. The method as claimed in claim 42, further comprising:

continually monitoring the offset position with an eye tracker.

44. The method as claimed in claim 33, wherein radiating in the centration beam in the form of one or more circles is implemented with a punctiform centration beam and a deflection movement is provided by a scanning system, and wherein the method further comprises an analysis of the back reflection of the centration beam radiated in as one or more circles, a positioning and/or orientation of a system axis of the UVL-LVC system relative to the patient's eye being determined on the basis of a deviation of the shape of the one or more circles of the back reflection from the shape of the circle or circles of the radiated-in radiation.

45. The method as claimed in claim 44, further comprising a determination of a correspondence of the system axis of the UVL-LVC system with the keratometric axis of the patient's eye when the deviation of the shape of the back reflection from the shape of the circle or circles of the radiated-in radiation is below a given threshold value or equal to zero.

46. The method as claimed in claim 44, further comprising a determination of a profile of the system axis of the UVL-LVC system through a vertex of the patient's eye when the deviation of the shape of the back reflection from the shape of the circle or circles of the radiated-in radiation is below a given threshold value or equal to zero.

47. The method as claimed in claim 45, further comprising an automated centration of the system axis of the UVL-LVC system on a vertex of the patient's eye or an automated centration of the system axis of the UVL-LVC system on a point of the patient's eye that deviates from the vertex and a determination of the deviating point of the patient's eye as an offset position.

48. The method as claimed in claim 47, further comprising:

determining adjusted coordinates for laser radiation to be radiated in for the treatment of the patient's eye whilst taking the offset position and the deviation from a centration according to the CSCLR condition connected therewith into account.

* * * * *